(12) United States Patent
Grigsby et al.

(10) Patent No.: US 11,413,451 B2
(45) Date of Patent: Aug. 16, 2022

(54) METHODS, SYSTEMS AND DEVICES FOR REDUCING MIGRATION

(71) Applicant: St. Jude Medical Luxembourg Holdings SMI S.A.R.L. ("SJM LUX SMI"), Luxembourg (LU)

(72) Inventors: Eric J. Grigsby, Napa, CA (US); Daniel M. Brounstein, San Francisco, CA (US); Fred I Linker, Los Altos, CA (US)

(73) Assignee: St. Jude Medical Luxembourg Holdings SMI S.A.R.L. ("SJM LUX SMI"), Luxembourg (LU)

( * ) Notice: Subject to any disclaimer, the term of this patent is extended or adjusted under 35 U.S.C. 154(b) by 50 days.

(21) Appl. No.: 16/579,389

(22) Filed: Sep. 23, 2019

(65) Prior Publication Data

US 2020/0016398 A1 Jan. 16, 2020

Related U.S. Application Data

(63) Continuation of application No. 15/178,012, filed on Jun. 9, 2016, now Pat. No. 10,456,576, which is a
(Continued)

(51) Int. Cl.
*A61N 1/05* (2006.01)
*A61N 1/18* (2006.01)
(Continued)

(52) U.S. Cl.
CPC ............ *A61N 1/0558* (2013.01); *A61N 1/05* (2013.01); *A61N 1/057* (2013.01); *A61N 1/0551* (2013.01);
(Continued)

(58) Field of Classification Search
CPC ...... A61N 1/05; A61N 1/0551; A61N 1/0558; A61N 1/057; A61N 1/0573; A61N 1/3752; A61N 1/36021
See application file for complete search history.

(56) References Cited

U.S. PATENT DOCUMENTS

| 525,891 A | 9/1894 | Fricke |
| 2,139,055 A | 12/1938 | Wright |

(Continued)

FOREIGN PATENT DOCUMENTS

| CN | 2401143 Y | 10/2000 |
| CN | 101594907 A | 12/2009 |

(Continued)

OTHER PUBLICATIONS

European Patent Office, Supplementary European Search Report for EP07759864 dated Nov. 27, 2012.
(Continued)

*Primary Examiner* — Jennifer Pitrak McDonald
*Assistant Examiner* — Pamela M. Bays
(74) *Attorney, Agent, or Firm* — Norton Rose Fulbright US LLP

(57) ABSTRACT

Devices, systems and methods for reducing migration of leads, catheters and similar devices are provided. In particular, devices, systems and methods are provided for creating a slack anchor which assists in maintaining the lead or catheter in a desired position. In some embodiments, the slack anchor is created within the epidural space. When targeting nerve anatomy within the spinal column or in the vicinity of the epidural space, anchoring within the epidural space allows the associated lead or catheter to be anchored as close to the target therapy site as desired or possible. By anchoring close to the target therapy site, the risk of movement or migration is significantly reduced or eliminated.

15 Claims, 10 Drawing Sheets

Related U.S. Application Data continuation of application No. 13/104,787, filed on May 10, 2011, now abandoned.

(60) Provisional application No. 61/333,199, filed on May 10, 2010.

(51) Int. Cl.
 *A61N 1/375* (2006.01)
 *A61N 1/36* (2006.01)

(52) U.S. Cl.
 CPC ........ *A61N 1/36021* (2013.01); *A61N 1/3752* (2013.01)

(56) References Cited

U.S. PATENT DOCUMENTS

| | | |
|---|---|---|
| 3,724,467 A | 4/1973 | Avery et al. |
| 3,845,770 A | 11/1974 | Theeuwes et al. |
| 3,916,899 A | 11/1975 | Theeuwes et al. |
| 4,141,367 A | 2/1979 | Ferreira |
| 4,232,679 A | 11/1980 | Schulman |
| 4,298,003 A | 11/1981 | Theeuwes et al. |
| 4,313,448 A | 2/1982 | Stokes |
| 4,374,527 A | 2/1983 | Iversen |
| 4,414,986 A | 11/1983 | Dickhudt et al. |
| 4,479,491 A | 10/1984 | Martin |
| 4,549,556 A | 10/1985 | Tarjan et al. |
| 4,559,951 A | 12/1985 | Dahl et al. |
| 4,573,481 A | 3/1986 | Bullara |
| 4,577,642 A | 3/1986 | Stokes |
| 4,590,946 A | 5/1986 | Loeb |
| 4,607,639 A | 8/1986 | Tanagho et al. |
| 4,739,764 A | 4/1988 | Lue et al. |
| 4,786,155 A | 11/1988 | Fantone et al. |
| 4,803,988 A | 2/1989 | Thomson |
| 4,920,979 A | 5/1990 | Bullara |
| 4,940,065 A | 7/1990 | Tanagho et al. |
| 4,950,270 A | 8/1990 | Bowman et al. |
| 4,976,711 A | 12/1990 | Parins et al. |
| 5,135,525 A | 8/1992 | Biscoping et al. |
| 5,138,138 A | 8/1992 | Theilacker et al. |
| 5,270,099 A | 12/1993 | Kamiyama et al. |
| 5,299,569 A | 4/1994 | Wernicke et al. |
| 5,344,438 A | 9/1994 | Testerman et al. |
| 5,344,439 A | 9/1994 | Otten |
| 5,358,514 A | 10/1994 | Schulman et al. |
| 5,370,644 A | 12/1994 | Langberg |
| 5,378,234 A | 1/1995 | Hammerslag et al. |
| 5,411,537 A | 5/1995 | Munshi et al. |
| 5,411,540 A | 5/1995 | Edell et al. |
| 5,417,208 A | 5/1995 | Winkler |
| 5,417,719 A | 5/1995 | Hull et al. |
| 5,419,763 A | 5/1995 | Hildebrand |
| 5,458,626 A | 10/1995 | Krause |
| 5,466,253 A | 11/1995 | Doan |
| 5,489,294 A | 2/1996 | McVenes et al. |
| 5,505,201 A | 4/1996 | Grill, Jr. et al. |
| 5,514,175 A | 5/1996 | Kim et al. |
| 5,584,835 A | 12/1996 | Greenfield |
| 5,634,462 A | 6/1997 | Tyler et al. |
| 5,643,330 A | 7/1997 | Holsheimer et al. |
| 5,702,429 A | 12/1997 | King |
| 5,711,316 A | 1/1998 | Elsberry et al. |
| 5,713,922 A | 2/1998 | King |
| 5,733,322 A | 3/1998 | Starkebaum |
| 5,741,319 A | 4/1998 | Woloszko et al. |
| 5,755,750 A | 5/1998 | Petruska et al. |
| 5,776,170 A | 7/1998 | MacDonald et al. |
| 5,807,339 A | 9/1998 | Bostrom et al. |
| 5,824,021 A | 10/1998 | Rise |
| 5,865,843 A | 2/1999 | Baudino |
| 5,871,531 A | 2/1999 | Struble |
| 5,885,290 A | 3/1999 | Guerrero et al. |
| 5,938,690 A | 8/1999 | Law et al. |
| 5,948,007 A | 9/1999 | Starkebaum et al. |
| 5,957,965 A | 9/1999 | Moumane et al. |
| 5,983,141 A | 11/1999 | Sluijter et al. |
| 5,984,896 A | 11/1999 | Boyd |
| 6,002,964 A | 12/1999 | Feler et al. |
| 6,044,297 A | 3/2000 | Sheldon et al. |
| 6,045,532 A | 4/2000 | Eggers et al. |
| 6,051,017 A | 4/2000 | Loeb et al. |
| 6,104,957 A | 8/2000 | Alo et al. |
| 6,120,467 A | 9/2000 | Schallhorn |
| 6,161,048 A | 12/2000 | Siuijter et al. |
| 6,175,764 B1 | 1/2001 | Loeb et al. |
| 6,181,965 B1 | 1/2001 | Loeb et al. |
| 6,185,455 B1 | 2/2001 | Loeb et al. |
| 6,205,359 B1 | 3/2001 | Boveja |
| 6,208,881 B1 | 3/2001 | Champeau |
| 6,208,902 B1 | 3/2001 | Boveja |
| 6,214,016 B1 | 4/2001 | Williams et al. |
| 6,259,952 B1 | 7/2001 | Siuijter et al. |
| 6,298,256 B1 | 10/2001 | Meyer |
| 6,314,325 B1 | 11/2001 | Fitz |
| 6,319,241 B1 | 11/2001 | King et al. |
| 6,349,233 B1 | 2/2002 | Adams |
| 6,353,762 B1 | 3/2002 | Baudino et al. |
| 6,356,786 B1 | 3/2002 | Rezai et al. |
| 6,360,750 B1 | 3/2002 | Gerber et al. |
| 6,366,814 B1 | 4/2002 | Boveja et al. |
| 6,393,325 B1 | 5/2002 | Mann et al. |
| 6,413,255 B1 | 7/2002 | Stern |
| 6,425,887 B1 | 7/2002 | McGuckin et al. |
| 6,438,423 B1 | 8/2002 | Rezai et al. |
| 6,440,090 B1 | 8/2002 | Schallhorn |
| 6,466,821 B1 | 10/2002 | Pianca et al. |
| 6,477,427 B1 | 11/2002 | Stolz et al. |
| 6,480,747 B2 | 11/2002 | Schmidt |
| 6,493,588 B1 | 12/2002 | Malaney et al. |
| 6,510,347 B2 | 1/2003 | Borkan |
| 6,512,958 B1 | 1/2003 | Swoyer et al. |
| 6,516,227 B1 | 2/2003 | Meadows et al. |
| 6,517,542 B1 | 2/2003 | Papay et al. |
| 6,522,926 B1 | 2/2003 | Kieval et al. |
| 6,535,767 B1 | 3/2003 | Kronberg |
| 6,582,441 B1 | 6/2003 | He et al. |
| 6,587,725 B1 | 7/2003 | Durand et al. |
| 6,605,094 B1 | 8/2003 | Mann et al. |
| 6,606,521 B2 | 8/2003 | Paspa et al. |
| 6,611,715 B1 | 8/2003 | Boveja |
| 6,625,496 B1 | 9/2003 | Ollivier |
| 6,638,276 B2 | 10/2003 | Sharkey et al. |
| 6,658,302 B1 | 12/2003 | Kuzma et al. |
| 6,714,822 B2 | 3/2004 | King et al. |
| 6,748,276 B1 | 6/2004 | Daignault, Jr. et al. |
| 6,754,539 B1 | 6/2004 | Erickson et al. |
| 6,788,975 B1 | 9/2004 | Whitehurst et al. |
| 6,792,318 B2 | 9/2004 | Chitre et al. |
| 6,832,115 B2 | 12/2004 | Borkan |
| 6,835,194 B2 | 12/2004 | Johnson et al. |
| 6,839,588 B1 | 1/2005 | Rudy |
| 6,849,075 B2 | 2/2005 | Bertolero et al. |
| 6,862,479 B1 | 3/2005 | Whitehurst et al. |
| 6,871,099 B1 | 3/2005 | Whitehurst et al. |
| 6,873,342 B2 | 3/2005 | Perry et al. |
| 6,889,094 B1 | 5/2005 | Kuzma et al. |
| 6,901,287 B2 | 5/2005 | Davis et al. |
| 6,902,547 B2 | 6/2005 | Aves et al. |
| 6,909,917 B2 | 6/2005 | Woods et al. |
| 6,928,320 B2 | 8/2005 | King |
| 6,971,391 B1 | 12/2005 | Wang et al. |
| 6,978,180 B2 | 12/2005 | Tadlock |
| 7,031,777 B2 | 4/2006 | Hine et al. |
| 7,047,082 B1 | 5/2006 | Schrom et al. |
| 7,069,083 B2 | 6/2006 | Finch et al. |
| 7,096,070 B1 | 8/2006 | Jenkins et al. |
| 7,127,287 B2 | 10/2006 | Duncan et al. |
| 7,146,222 B2 | 12/2006 | Boling |
| 7,181,289 B2 | 2/2007 | Pflueger et al. |
| 7,333,857 B2 | 2/2008 | Campbell |
| 7,337,005 B2 | 2/2008 | Kim et al. |
| 7,337,006 B2 | 2/2008 | Kim et al. |

(56) References Cited

U.S. PATENT DOCUMENTS

| | | |
|---|---|---|
| 7,447,546 B2 | 11/2008 | Kim et al. |
| 7,450,993 B2 | 11/2008 | Kim et al. |
| 7,502,651 B2 | 3/2009 | Kim et al. |
| 7,555,349 B2 | 6/2009 | Wessman et al. |
| 7,580,753 B2 | 8/2009 | Kim et al. |
| 7,672,736 B2 | 3/2010 | Boling |
| 9,844,661 B2 | 12/2017 | Goldmen et al. |
| 2001/0003799 A1 | 6/2001 | Boveja |
| 2001/0006967 A1 | 7/2001 | Crain et al. |
| 2002/0064841 A1 | 5/2002 | Klemic et al. |
| 2002/0077684 A1 | 6/2002 | Clemens et al. |
| 2002/0087113 A1 | 7/2002 | Hartlaub |
| 2002/0099430 A1 | 7/2002 | Verness |
| 2002/0116030 A1 | 8/2002 | Rezai |
| 2002/0128694 A1 | 9/2002 | Holsheimer |
| 2002/0143377 A1 | 10/2002 | Wessman et al. |
| 2002/0147486 A1 | 10/2002 | Soukup et al. |
| 2002/0198527 A1 | 12/2002 | Muckter |
| 2003/0018367 A1 | 1/2003 | DiLorenzo |
| 2003/0023241 A1 | 1/2003 | Drewry et al. |
| 2003/0045919 A1 | 3/2003 | Swoyer et al. |
| 2003/0060868 A1 | 3/2003 | Janke |
| 2003/0069569 A1 | 4/2003 | Burdette et al. |
| 2003/0078633 A1 | 4/2003 | Firlik et al. |
| 2003/0088301 A1 | 5/2003 | King |
| 2003/0100933 A1 | 5/2003 | Ayal et al. |
| 2003/0114905 A1 | 6/2003 | Kuzma |
| 2003/0130577 A1 | 7/2003 | Purdy et al. |
| 2003/0144657 A1 | 7/2003 | Bowe et al. |
| 2003/0144709 A1 | 7/2003 | Zabara et al. |
| 2003/0181958 A1 | 9/2003 | Dobak |
| 2003/0187490 A1 | 10/2003 | Gliner |
| 2003/0195602 A1 | 10/2003 | Boling |
| 2003/0220677 A1 | 11/2003 | Doan et al. |
| 2003/0236562 A1 | 12/2003 | Kuzma |
| 2004/0015202 A1 | 1/2004 | Chandler et al. |
| 2004/0019359 A1 | 1/2004 | Worley et al. |
| 2004/0019369 A1 | 1/2004 | Duncan et al. |
| 2004/0059404 A1 | 3/2004 | Bjorklund et al. |
| 2004/0064173 A1 | 4/2004 | Hine et al. |
| 2004/0116977 A1* | 6/2004 | Finch ............. A61N 1/36021 607/46 |
| 2004/0122360 A1 | 6/2004 | Waldhauser et al. |
| 2004/0122477 A1 | 6/2004 | Whitehurst et al. |
| 2004/0122497 A1 | 6/2004 | Zhang et al. |
| 2004/0122498 A1 | 6/2004 | Zhang et al. |
| 2004/0147992 A1 | 7/2004 | Bluger et al. |
| 2004/0210290 A1 | 10/2004 | Omar-Pasha |
| 2004/0215286 A1 | 10/2004 | Stypulkowski |
| 2004/0230273 A1 | 11/2004 | Cates et al. |
| 2004/0230280 A1 | 11/2004 | Cates et al. |
| 2004/0243210 A1 | 12/2004 | Morgan et al. |
| 2005/0027338 A1 | 2/2005 | Hill |
| 2005/0027339 A1 | 2/2005 | Schrom et al. |
| 2005/0027340 A1 | 2/2005 | Schrom et al. |
| 2005/0027341 A1 | 2/2005 | Schrom et al. |
| 2005/0033295 A1 | 2/2005 | Wisnewski |
| 2005/0033393 A1 | 2/2005 | Daglow |
| 2005/0038489 A1 | 2/2005 | Grill |
| 2005/0070982 A1 | 3/2005 | Heruth et al. |
| 2005/0080325 A1 | 4/2005 | Erickson |
| 2005/0090885 A1 | 4/2005 | Harris et al. |
| 2005/0096718 A1 | 5/2005 | Gerber et al. |
| 2005/0149154 A1 | 7/2005 | Cohen et al. |
| 2005/0159799 A1 | 7/2005 | Daglow et al. |
| 2005/0203599 A1 | 9/2005 | Garabedian et al. |
| 2005/0222647 A1 | 10/2005 | Wahlstrand et al. |
| 2005/0251237 A1 | 11/2005 | Kuzma et al. |
| 2005/0288761 A1 | 12/2005 | Brabec et al. |
| 2006/0004364 A1 | 1/2006 | Green et al. |
| 2006/0009820 A1 | 1/2006 | Royle |
| 2006/0052827 A1 | 3/2006 | Kim et al. |
| 2006/0052836 A1 | 3/2006 | Kim et al. |
| 2006/0052839 A1 | 3/2006 | Kim et al. |
| 2006/0052856 A1 | 3/2006 | Kim et al. |
| 2006/0064150 A1 | 3/2006 | Heist et al. |
| 2006/0089609 A1 | 4/2006 | Bleich et al. |
| 2006/0089691 A1 | 4/2006 | Kaplan et al. |
| 2006/0089695 A1 | 4/2006 | Bolea et al. |
| 2006/0089696 A1 | 4/2006 | Olsen et al. |
| 2006/0089697 A1 | 4/2006 | Cross et al. |
| 2006/0094976 A1 | 5/2006 | Bleich |
| 2006/0095088 A1 | 5/2006 | De Ridder |
| 2006/0111768 A1 | 5/2006 | Wessman et al. |
| 2006/0155344 A1 | 7/2006 | Rezai et al. |
| 2006/0161235 A1 | 7/2006 | King |
| 2006/0167525 A1 | 7/2006 | King |
| 2006/0195169 A1 | 8/2006 | Gross et al. |
| 2006/0200121 A1 | 9/2006 | Mowery |
| 2006/0206118 A1 | 9/2006 | Kim et al. |
| 2006/0241716 A1 | 10/2006 | Finch et al. |
| 2006/0241734 A1 | 10/2006 | Marshall et al. |
| 2006/0041295 A1 | 12/2006 | Osypka |
| 2007/0043400 A1 | 2/2007 | Donders et al. |
| 2007/0060954 A1 | 3/2007 | Cameron et al. |
| 2007/0123954 A1 | 5/2007 | Gielen et al. |
| 2007/0179579 A1 | 8/2007 | Feler et al. |
| 2007/0213671 A1 | 9/2007 | Hiatt |
| 2007/0255366 A1 | 11/2007 | Gerber et al. |
| 2007/0270928 A1 | 11/2007 | Erlebacher |
| 2007/0276319 A1 | 11/2007 | Betts |
| 2008/0009927 A1 | 1/2008 | Vilims |
| 2008/0033431 A1 | 2/2008 | Jung et al. |
| 2008/0039916 A1 | 2/2008 | Colliou et al. |
| 2008/0103572 A1 | 5/2008 | Gerber |
| 2008/0103579 A1 | 5/2008 | Gerber |
| 2008/0103580 A1 | 5/2008 | Gerber |
| 2008/0119711 A1 | 5/2008 | Nikumb et al. |
| 2008/0140152 A1 | 6/2008 | Imran et al. |
| 2008/0140153 A1 | 6/2008 | Burdulis |
| 2008/0140169 A1 | 6/2008 | Imran |
| 2008/0147156 A1 | 6/2008 | Imran |
| 2008/0154349 A1 | 6/2008 | Rossing |
| 2008/0167698 A1 | 7/2008 | Kim et al. |
| 2008/0183221 A1 | 7/2008 | Burdulis |
| 2008/0183257 A1* | 7/2008 | Imran ............. A61N 1/0558 607/117 |
| 2008/0188916 A1 | 8/2008 | Jones et al. |
| 2009/0204173 A1 | 8/2009 | Fang et al. |
| 2009/0210041 A1 | 8/2009 | Kim et al. |
| 2009/0248095 A1 | 10/2009 | Schleicher et al. |
| 2009/0270960 A1 | 10/2009 | Zhao et al. |
| 2009/0299444 A1 | 12/2009 | Boling |
| 2010/0121408 A1 | 5/2010 | Imran et al. |
| 2010/0137938 A1 | 6/2010 | Kishawi et al. |
| 2010/0179562 A1 | 7/2010 | Linker et al. |
| 2010/0191307 A1 | 7/2010 | Fang et al. |
| 2010/0249875 A1 | 9/2010 | Kishawi et al. |
| 2010/0292769 A1 | 11/2010 | Braunstein et al. |
| 2011/0184486 A1 | 7/2011 | De Ridder |
| 2012/0158094 A1 | 6/2012 | Kramer et al. |
| 2012/0283800 A1 | 11/2012 | Perryman et al. |
| 2012/0310140 A1 | 12/2012 | Kramer et al. |
| 2012/0330384 A1 | 12/2012 | Perryman et al. |
| 2013/0066400 A1 | 3/2013 | Perryman et al. |
| 2014/0031837 A1 | 1/2014 | Perryman et al. |
| 2014/0343624 A1 | 11/2014 | Kramer |

FOREIGN PATENT DOCUMENTS

| | | |
|---|---|---|
| CN | 101678204 A | 3/2010 |
| EP | 0779080 A | 6/1997 |
| EP | 1304135 A2 | 4/2003 |
| EP | 2756864 A1 | 7/2014 |
| JP | 03041191 B2 | 6/1991 |
| JP | H06-218064 A | 8/1994 |
| JP | 8500996 A | 2/1996 |
| JP | 8080353 A | 3/1996 |
| JP | 10243954 A | 9/1998 |
| JP | 2004512105 | 4/2004 |
| JP | 2006523215 | 10/2004 |
| JP | 2005516697 | 6/2005 |
| JP | 2006508768 A | 3/2006 |
| JP | 2008526299 | 7/2008 |

(56) References Cited

FOREIGN PATENT DOCUMENTS

| | | |
|---|---|---|
| JP | 2009539425 A | 11/2009 |
| JP | 2009539426 A | 11/2009 |
| WO | WO-02/096512 A1 | 12/2002 |
| WO | WO-03/018113 A1 | 3/2003 |
| WO | WO-03/043690 A1 | 5/2003 |
| WO | WO-03/063692 A2 | 8/2003 |
| WO | WO-03/066154 A2 | 8/2003 |
| WO | WO-03/084433 A2 | 10/2003 |
| WO | WO-03/090599 A2 | 11/2003 |
| WO | WO-2005/092432 A1 | 10/2005 |
| WO | WO-2006/033039 A1 | 3/2006 |
| WO | WO-2006/084635 A2 | 8/2006 |
| WO | WO-2008/094952 A2 | 8/2008 |
| WO | WO-2009/134350 A2 | 11/2009 |

OTHER PUBLICATIONS

Bernstein et al. A Prospective Clinical Evaluation of a Rechargeable IPG: An Interim Analysis of Sustainability of Treatment: (Presentation Abstract): North American Neuromodulation Society; Abs. No. 2010-A-132-NANS; p. 126; Las Vegas, NV.; Dec. 2-5, 2010.
Kishawi et al.; U.S. Appl. No. 14/615,281 entitled "Pain management with stimulation subthreshold to paresthesia," filed Feb. 5, 2015.
Horsch, S. et al. Epidural spinal cord stimulation in the treatment of severe peripheral arterial occlusive disease; Annals of Vascular Surgery; 8(5): 468-74. Sep. 1994.
Mayfield Clinic for Brain & Spine; printed from http://www.mayfieldclinic.com/PE-AnatSpine.htm (last updated Jan. 2013); 7 pages.
medicinenet.com; Definition of Lateral; printed from http://www.medterms.com/script/main/art.asp?articlekey=6226 (on Jun. 4, 2014); 3 pages.
Kim et al.; U.S. Appl. No. 14/216,805 entitled "Neurostimulation System," filed Mar. 17, 2014.
Cipolla—The Cerebral Circulation. Chap. 3—Perivascular Innervation; Morgan & Claypool Life Sciences; San Rafael, CA.; 1(1):pp. 3; Jan. 2009.
Dorsal Root Ganglion; www.biology-online.org/dDorsal_root_ganglion; downloaded Nov. 5, 2013; 4 pgs.
The Peripheral Nervous System; http://cnx.org/content/m44751/latest; downloaded Nov. 5, 2013; 7 pgs.
Truijen et al.; Parasympathetic control of blood flow to the activated human brain; Exp. Physiol.; 95(10):980-981; Oct. 2010.
Burdulis; U.S. Appl. No. 13/975,083 entitled "Hard Tissue Anchors and Delivery Devices," filed Aug. 23, 2013.
Wedley et al. Handbook of Clinical Techniques in the Management of Chronic Pain. Taylor & Francis; pp. 17-19. Nov. 27, 1996.
Kim et al.: U.S. Appl. No. 13/706,100 entitled "Neurostimulation Methods And Systems," filed Dec. 5, 2012.
Kishawi et al.; U.S. Appl. No. 13/753,326 entitled "Pain management with stimulation subthreshold to paresthesia," filed Jan. 29, 2013.
Kramer et al.; U.S. Appl. No. 13/458,697 entitled "Selective stimulation to modulate the sympathetic nervous system," filed Apr. 27, 2012.
Kim et al.; U.S. Appl. No. 13/550,439 entitled "Methods For Stimulating A Dorsal Root Ganglion," filed Jul. 16, 2012.
Kim et al.; U.S. Appl. No. 13/402,786 entitled "Neurostimulation System," filed Feb. 22, 2012.
Clark, R. K. "Anatomy and physiology: understanding the human body," Jones & Bartlett Publishers; Sudbury, MA; ISBN 0-7637-4816-6; Chapter 12; pp. 213-215; Feb. 28, 2005.
Abdulla et al. 2001. Axotomy- and autotomy-induced changes in the excitability of rat dorsal root ganglion neurons; J. Neurophysiol.; 85(2); pp. 630-643.
Advanced Neuromodulation Systems, Inc. (ANSI) Research Briefing dated Aug. 20, 2004 by Stephens Inc. Investment Bankers, pp. 1-4.
Advanced Neuromodulation Systems, Inc. (ANSI) Research Bulletin dated Jul. 2, 2004 by Stephens Inc. Investment Bankers, pp. 1-7.
Advanced Neuromodulation Systems, Inc. (ANSI) Research Bulletin dated Jul. 27, 2004 by Stephens Inc. Investment Bankers, pp. 1-9.
Advanced Neuromodulation Systems, Inc. Equity Research dated Jan. 16, 2003 by Pacific Growth Equities, pp. 1-8.
Alo, K. M. 2002. New Trends in Neuromodulation for the Management of Neuropathic Pain. Neurosurgery. 50 (4): 690-703.
Aoki, Y. et al. 2004. Distribution and Immunocytochemical Characterization of Dorsal Root Ganglion Neurons Innervating the Lumbar Intervertebral Disc in Rats: A Review. Life Sciences. 74 (21): 2627-2642.
Askar, Z. et al. 2003. Scott Wiring for Direct Repair of Lumbar Spondylolysis. Spine. 28 (4): 354-357.
Baba, H. et al. 1999. Peripheral Inflammation Facilitates Aβ Fiber-Mediated Synaptic Input to the Substantia Gelatinosa of the Adult Rat Spinal Cord. The Journal of Neuroscience. 19 (2): 859-867.
Bajwa, Z. H. et al. 2001. Herpetic Neuralgia: Use of Combination Therapy for Pain Relief in Acute and Chronic Herpes Zoster. Geriatrics. 56 (12): 18-24.
Barendse, G. A. et al. 2001. Randomized Controlled Trial of Percutaneo Intradiscal Radiofrequency Thermocoagulation for Chronic Discogenic Back Pain: Lack of Effect From a 90-Second 70 C Lesion. Spine. 26 (3): 287-92. (Abstract Only).
Barlocher, C. B. et al. 2003. Kryorhizotomy: An Alternative Technique for Lumbar Medial Branch Rhizotomy in Lumbar Facet Syndrome. J. Neurosurg. 98 (1): 14-20. (Abstract Only).
Blau, A. et al. 1997. Characterization and Optimization of Microelectrode Arrays for In Vivo Nerve Signal Recording and Stimulation. Biosens. Bioelectron. 12 (9-10): 883-92. (Abstract Only).
Boston Scientific A Neuromodulation Primer dated Jun. 9, 2004 in Medical Supplies and Devices, published by Susquehanna Financial Group, LLLP, pp. 1-17.
Brammah, T. B. et al. 1994. Syringomyelia as a Complication of Spinal Arachnoiditis. Spine. 19 (22): 2603-5. (Abstract Only).
Braverman D. L. et al. 2001. Using Gabapentin to Treat Failed Back Surgery Syndrome Caused by Epidural Fibrosis: A Report of 2 Cases. Arch. Phys. Med. Rehabil. 82 (5): 691-3. (Abstract Only).
Burton et al. The organization of the seventh lumbar spinal ganglion of the cat; J. Comp. Neurol.; 149(2); pp. 215-232; May 15, 1973.
Carlton, S. M. et al. 2001. Tonic Control of Peripheral Cutaneo Nociceptors by Somatostatin Receptors. Journal of Neuroscience. 21 (11): 4042-4049.
Chaplan, S. R. et al. 1994. Quantitative Assessment of Tactile Allodynia in the Rat Paw. Journal of Neuroscience Methods. 53 (1): 55-63.
Cho, J. 1997. Percutaneo Radiofrequency Lumbar Facet Rhizotomy in Mechanical Low Back Pain Syndrome. Stereotact Funct Neurosurg. 68 (1-4): 212-7. (Abstract Only).
Crampon, M.-A. et al. 2002. Nerve Cuff Electrode With Shape Memory Alloy Armature: Design and Fabrication. Bio-Medical Materials and Engineering. 12 (4): 397-410.
Cuoco, Jr., Frank A. et al. 2000. Measurement of External Pressures Generated by Nerve Cuff Electrodes. IEEE Transactions on Rehabilitation Engineering. 8 (1): 35-41.
Cyberonics, Inc. Equity Research dated Jan. 16, 2003 by Pacific Growth Equities, pp. 1-14.
Denny, N. M. et al. 2003. Evaluation of an Insulated Tuohy Needle System for the Placement of Interscalene Brachia! Plex Catheters. Anaesthesia. 58 (6): 554-7. (Abstract Only).
Dreyfuss, P. et al. 2000. Efficacy and Validity of Radiofrequency Neurotomy for Chronic Lumbar Zygapophysial Joint Pain. Spine. 25 (10): 1270-1277.
Dubuisson, D. 1995. Treatment of Occipital Neuralgia by Partial Posterior Rhizotomy at C1-3. J. Neurosurg. 82 (4): 581-6. (Abstract Only).
Eschenfelder, S. et al. 2000. Dorsal Root Section Elicits Signs of Neuropathic Pain Rather than Reversing Them in Rats With L5 Spinal Nerve Injury. Pain. 87 (2): 213-219.
Firth, A. et al. 1999. Development of a Scale to Evaluate Postoperative Pain in Dogs. J. Am. Vet. Med. Assoc. 214 (5): 651-659.

(56) References Cited

OTHER PUBLICATIONS

Garcia Cosamalon, P. J. et al. 1991. Dorsal Percutaneo Radiofrequency Rhizotomy Guided With CT Scan in Intercostal Neuralgias. Technical note. Acta Neurochir (Wien). 109 (3-4): 140-1.
Giorgi, C. et al. 1984. Surgical Treatment of Glossopharyngeal Neuralgia and Pain From Cancer of the Nasopharynx. A 20-Year Experience. J. Neurosurg. 61 (5): 952-5. (Abstract Only).
Gocer, A. I. et al. 1997. Percutaneo Radiofrequency Rhizotomy of Lumbar Spinal Facets: The results of 46 cases. Neurosurg. Rev. 20 (2): 114-6. (Abstract Only).
Haller, H. et al. Treatment of Chronic Neuropathic Pain After Traumatic Central Cervical Cord Lesion with Gabapentin. Journal of Neural Transmission. 110 (9): 977-981.
Herron, L. D. 1989. Selective Nerve Root Block in Patient Selection for Lumbar Surgery: Surgical Results. J. Spinal Disord. 2 (2): 75-9. (Abstract Only).
Higuchi, Y. et al. 2002. Exposure of the Dorsal Root Ganglion in Rats to Pulsed Radiofrequency Currents Activates Dorsal Horn Lamina I and II Neurons. Neurosurgery. 50 (4): 850-856.
Holsheimer, J. et al. 1995. Effects of Electrode Geometry and Combination on Nerve Fibre Selectivity in Spinal Cord Stimulation. Medical & Biological Engineering & Computing. 33 (5): 676-682.
Igarashi, T. et al. 2004. Lysis of Adhesions and Epidural Injection of Steroid/Local Anaesthetic During Epiduroscopy Potentially Alleviate Low Back and Leg Pain in Elderly Patients With Lumbar Spinal Stenosis. British Journal of Anaesthesia. 93 (2): 181.
Julius, David et al. 2001. Molecular Mechanisms of Nociception. Nature. 413 (6852): 203-210.
Kanpolat, Y. et al. 2001. Percutaneo Controlled Radiofrequency Trigeminal Rhizotomy for the Treatment of Idiopathic Trigeminal Neuralgia: 25-Year Experience with 1600 Patients. Neurosurgery. 48 (3): 524-534.
Kapadia, N. P. et al. 2000. Gabapentin for Chronic Pain in Spinal Cord Injury: A Case Report. Arch. Phys. Med. Rehabil. 81 (10): 1439-41. (Abstract Only).
Kapoor, V. et al. 2003. Refractory Occipital Neuralgia: Preoperative Assessment With CT-Guided Nerve Block Prior to Dorsal Cervical Rhizotomy. American Journal of Neuroradiology. 24 (10): 2105-10.
Karai, L. et al. 2004. Deletion of Vanilloid Receptor 1-Expressing Primary Afferent Neurons for Pain Control. Journal of Clinical Investigation. 113 (9): 1344-1352.
Kline, D. G. et al. 1998. Management and Results of Sciatic Nerve Injuries: A 24-Year Experience. Journal of Neurosurgery. 89 (1): 13-23.
Kobayashi, S. et al. 2004. Pathology of Lumbar Nerve Root Compression Part 1: Intraradicular Inflammatory Changes Induced by Mechanical Compression. Journal of Orthopaedic Research. 22 (1): 170-179.
Kobayashi, S. et al. 2004. Pathology of Lumbar Nerve Root Compression Part 2: Morphological and Immunohistochemical Changes of Dorsal Root Ganglion. Journal of Orthopaedic Research. 22(1): 180-188.
Kocsis et al. NR2B receptors are involved in the mediation of spinal segmental reflex potentials but not in the cumulative motoneuronal depolarization in vitro; Brain Research Bulletin, Elsevier Science Ltd.; vol. 64; No. 2; pp. 133-138; Aug. 30, 2004.
Koszewski, W. et al. 2003. The DREZ Lesion as an Effective Treatment for Chronic Hypothetically Post-Herpetic Neuropathic Pain. Case Report and Review of Literature. Neurol. Neurochir. Pol. 37 (4): 943-53. (Abstract Only).
Lawrence, S. M. et al. 2002. Long-Term Biocompatibility of Implanted Polymer-Based Intrafascicular Electrodes. Journal of Biomedical Materials Research. 63 (5): 501-506.
Lee, In-Seop et al. 2002. Characterization of Iridium Film as a Stimulating Neural Electrode. Biomaterials. 23 (11): 2375-2380.
Lew, H. L. et al. 2004. Preganglionic Approach to Transforaminal Epidural Steroid Injections. Am. J. Phys. Med. Rehabil. 83 (5): 378.
Lopez et al.; Excitatory and inhibitory effects of serotonin on spinal nociceptive reflexes are mediated by 5-HT2 and 5-HT1B receptors;

(Database Biosis Biosciences Information Service, Philadelphia, PA, US, XP002567533, accession No. PREV200100573757); Abstract; 2001.
Ma et al. 2005. Enhanced excitability of dissociated primary sensory neurons after chronic compression of the dorsal root ganglion in the rat; Pain; 113 (1-2); pp. 106-112.
Maher, C. O. et al. 1999. Lateral Exit-Zone Stenosis and Lumbar Radiculopathy. J. Neurosurg. 90 (1): 52-8. (Abstract Only).
Mailley, S. et al. 2004. Thin Film Platinum Cuff Electrodes for Neurostimulation: In Vitro Approach of Safe Neurostimulation Parameters. Bioelectrochemistry. 63: 359-364.
Masini, M. et al. 1996. Activated Pyrolytic Carbon Tip Pacing Leads: An Alternative to Steroid-Eluting Pacing Leads? PACE. 1: 1832-1835.
Medtronic, Inc. Equity Research dated Dec. 18, 2002 by Pacific Growth Equities, pp. 1-20.
Medtronic. Analysis of Sales/Earnings—F1Q05: Many Gives and Takes in the Quarter dated Aug. 20, 2004 by Morgan Stanley, pp. 1-25.
Methods of Placement of Neurostimulation Lead, Infusion, Catheter, and/or Sensor Via Peripheral Vasculature. From IP.com PriorArtDatabase—Apr. 10, 2003—#000012136 http://www.priorartdatabase.com/IPCOM/000012136.
Modern Ideas: The Gate Control Theory of Chronic Pain. Spine-Health.com: Your Comprehensive Resource for Back Pain. http://www.spine-health.com/topics/cd/pain/chronic_pain_theories/chronic_pain_theory02.html (accessed Feb. 24, 2006).
Mono, H. G. et al. 2004. Implantable Transveno Pacing Leads: The Shape of Things to Come. Pace. 27: 887-893.
Monti, E. 2004. Peripheral Nerve Stimulation: A Percutaneo Minimally Invasive Approach. Neuromodulation. 7 (3): 193. (Abstract Only).
Myles et al. 1992. Effects of different methods of peripheral nerve repair on the number and distribution of muscle afferent neurons in rat dorsal root ganglion; J. Neurosurg: 77(3); pp. 457-462.
Nannini et al. 1991. Muscle recruitment with intrafascicular electrodes; IEEE Trans. on Biomedical Engineering; vol. 38; No. 8; pp. 769-776.
Naples, G. G. 1988. A Spiral Nerve Cuff Electrode for Peripheral Nerve Stimulation. IEEE Transactions on Biomedical Engineering. 35 (11): 905-916.
Narozny, M. et al. 2001. Therapeutic Efficacy of Selective Nerve Root Blocks in the Treatment of Lumbar Radicular Leg Pain. Swiss Med. Wkly. 131 (5-6): 75-80.
Nashold, B. S. et al. 1979. Peripheral Nerve Stimulation for Pain Relief Using a Multicontact Electrode System. Technical note. Journal of Neurosurgery. 51 (6): 872-873.
Nashold, B. S. et al. 1982. Long-Term Pain Control by Direct Peripheral-Nerve Stimulation. The Journal of Bone and Joint Surgery. 64 (1): 1-10.
Neumann, S. et al. 2002. Regeneration of Sensory Axons Within the Injured Spinal Cord Induced by Intraganglionic cAMP Elevation. Neuron. 34 (6): 885-93.
Nielson, K. D. et al. 1976. Peripheral Nerve Injury From Implantation of Chronic Stimulating Electrodes for Pain Control. Surg. Neural. 5 (1): 51-3. (Abstract Only).
North, R. B. et al. 1991. Dorsal Root Ganglionectomy for Failed Back Surgery Syndrome: A 5-Year Follow-Up Study. J. Neurosurg. 74: 236-242.
North, R. B. et al. 2000. Chapter 123: Current Concepts in the Neurosurgical Management of Persistent Pain (pp. 1634-1637). Operative Neurosurgical Techniques 4th Edition (Henry H. Schmidek et al. eds.). Philadelphia: W.B. Saunders Company.
Nygaard, O. P. et al. 1998. The Function of Sensory Nerve Fibers in Lumbar Radiculopathy: Use of Quantitative Sensory Testing in the Exploration of Different Populations of Nerve Fibers and Dermatomes. Spine. 23 (3): 348-352.
Obata, K. et al. 2004. Activation of Extracellular Signal-Regulated Protein Kinase in the Dorsal Root Ganglion Following Inflammation Near the Nerve Cell Body. Neuroscience. 126 (4): 1011-1021.
Obata, K. et al. 2002. Expression of Neurotrophic Factors in the Dorsal Root Ganglion in a Rat Model of Lumbar Disc Herniation. Pain. 99 (1-2): 121-132.

(56) References Cited

OTHER PUBLICATIONS

Olby, N. J. et al. 2001. Development of a Functional Scoring System in Dogs With Acute Spinal Cord Injuries. Am. J. Vet. Res. 62 (10): 1624-1628.
Parlier-Cuau, C. et al. 1999. Symptomatic Lumbar Facet Joint Synovial Cysts: Clinical Assessment of Facet Joint Steroid Injection After 1 and 6 Months and Long-Term Follow-Up in 30 Patients. Radiology. 210 (2): 509-513.
Pedrolli, C. et al. 1990. Dorsolumbar Arachnoid Cysts. A Case Report. Recenti Prog. Med. 81 (11): 699-701. (Abstract Only).
Prats-Galino et al. 1999. Representations of hindlimb digits in rat dorsal root ganglia: J. Comp. Neurol; 408 (1); pp. 137-145.
Rodriguez, F. J. et al. 2000. Polyimide Cuff Electrodes for Peripheral Nerve Stimulation. Journal of Neuroscience Methods. 98 (2): 105-118.
Rokugo, T. et al. 2002. A Histochemical Study of Substance P in the Rat Spinal Cord: Effect of Transcutaneo Electrical Nerve Stimulation. J. Nippon Med. Sch. 69 (5): 428-433.
Romero, E. et al. 2001. Neural Morphological Effects of Long-Term Implantation of the Self-Sizing Spiral Cuff Nerve Electrode. Medical & Biological Engineering & Computing. 39 (1): 90-100.
Rongstad, K. et al. 1996. Popliteal Sciatic Nerve Block for Postoperative Analgesia. Foot Ankle Int. 17 (7): 378-82. (Abstract Only).
Ruetten, S. et al. 2003. Endoscopic Surgery of the Lumbar Epidural Space (Epiduroscopy): Results of Therapeutic Intervention in 93 Patients. Minim. Invasive Neurosurg. 46 (1): 1-4. (Abstract Only).
Sairyo, K. et al. 2003. A New Endoscopic Technique to Decompress Lumbar Nerve Roots Affected by Spondylolysis. Technical Note. J. Neurosurg. 98 (3): 290-3. (Abstract Only).
Saris, S. C. et al. 1986. Sacrococcygeal Rhizotomy for Perineal Pain. Neurosurgery. 19 (5): 789-93. (Abstract Only).
Sauvage, P. J. et al. 2000. Intraspinal Synovial Cysts of the Lumbar Spine: Imaging Findings and Treatment by Percutaneo Steroid Injection. Review of 13 Cases. Journal de Radiologie 81 (1): 33-8.
Schwartzman, R. J. et al. 2001. Neuropathic Central Pain: Epidemiology, Etiology, and Treatment Options. Arch. Neurol. 58 (10): 1547-1550.
Sedan, R. et al. 1978. Therapeutic Electrical Neurostimulation. French Language Society of Neurosurgery—28th Annual Congress—Athens, May 29-30, 1978. Neurochirurgie. 24 Suppl. 1:1-138 (in French with English Summary) pp. 121-125.
Sheth, R. N. et al. 2002. Mechanical Hyperalgesia After an L5 Ventral Rhizotomy or an L5 Ganglionectomy in the Rat. Pain. 96: 63-72.
Siddall, P. J. et al. 2004. Persistent Pain as a Disease Entity: Implications for Clinical Management. Anesth. Analg. 99: 510-20.
Silvers, H. R. 1990. Lumbar Percutaneo Facet Rhizotomy. Spine.15 (1): 36-40. (Abstract Only).
Slappendel, R. et al. 1997. The efficacy of Radiofrequency Lesioning of the Cervical Spinal Dorsal Root Ganglion in a Double Blinded Randomized Study: No difference Between 40 Degrees C and 67 Degrees C Treatments. Pain. 73 (2): 159-63. (Abstract Only).
Sluijter, M. E. et al. 1998. The Effects of Pulsed Radiofrequency Fields Applied to the Dorsal Root Ganglion—A Preliminary Report. The Pain Clinic. 11 (2): 109-117.
Smith, H. P. et al. 1981. Radiofrequency Neurolysis in a Clinical Model: Neuropathological Correlation. J. Neurosurg. 55 (2): 246-53. (Abstract Only).
Spaic, M. et al. 1999. Drez Surgery on Conus Medullaris (After Failed Implantation of Vascular Omental Graft) for Treating Chronic Pain Due to Spine (Gunshot) Injuries. Acta Neurochir (Wein). 141 (12): 1309-1312.
Spaic, M. et al. 2002. Microsurgical DREZotomy for Pain of Spinal Cord and Cauda Equina Injury Origin: Clinical Characteristics of Pain and Implications for Surgery in a Series of 26 Patients. Acta Neurochir (Wien). 144 (5): 453-462.
Stanton-Hicks, M. et al. 1997. Stimulation of the Central and Peripheral Nervous System for the Control of Pain. Journal of Clinical Neurophysiology. 14 (1): 46-62.
Steinbok, P. et al. 1998. Complications After Selective Posterior Rhizotomy for Spasticity in Children With Cerebral Palsy. Pediatr. Neurosurg. 28 (6): 300-13. (Abstract Only).
Stolker, R. J. et al. 1994. The Treatment of Chronic Thoracic Segmental Pain by Radiofrequency Percutaneo Partial Rhizotomy. J. Neurosurg. 80: 986-992.
Strait, T. A. et al. 1981. Intraspinal Extradural Sensory Rhizotomy in Patients With Failure of Lumbar Disc Surgery. J. Neurosurg. 54 (2): 193-6. (Abstract Only).
Taha, J. M. et al. 1995. Long-Term Results of Radiofrequency Rhizotomy in the Treatment of Cluster Headache. Headache. 35 (4): 193-6. (Abstract Only).
Taub, A. et al. 1995. Dorsal Root Ganglionectomy for Intractable Monoradicular Sciatica: A Series of 61 Patients. Stereotact Funct Neurosurg. 65 (14): 106-110.
Uematsu, S. 1988. Chapter 106: Percutaneo Electrothermocoagulation of Spinal Nerve Trunk, Ganglion, and Rootlets (pp. 1207-1221). Operative Neurosurgical Techniques, Indications, Methods and Results 2nd edition. (Henry H. Schmidek et al. eds.).
Van Zundert, J. et al. 2005. Pulsed Radiofrequency in Chronic Pain Management: Looking for the Best Use of Electrical Current. World Institute of Pain. 5 (2): 74-76.
Van De Kraats, E. B. et al. 2004. Noninvasive Magnetic Resonance to Three-Dimensional Rotational X-Ray Registration of Vertebral Bodies for Image-Guided Spine Surgery. Spine. 29 (3): 293-297.
Van Kleef, M. et al. 1993. Effects and Side Effects of a Percutaneo Thermal Lesion of the Dorsal Root Ganglion in Patients with Cervical Pain Syndrome. Pain. 52 (1): 49-53.
Van Kleef, M. et al. 1996. Radiofrequency Lesion Adjacent to the Dorsal Root Ganglion for Cervicobrachial Pain: A Prospective Double Blind Randomized Study. Neurosurgery. 38 (6): 1127-31.
Van Kleef, M. et al. 1998. Chapter 160: Radiofrequency Lesions in the Treatment of Pain of Spinal Origin (pp. 1585-1599). Textbook of Stereotactic and Functional Neurosurgery 1st Edition. (Philip L. Gildenberg et al. eds.). New York: McGraw-Hill.
Van Zundert, J. et al. 2005. Pulsed and Continuous Radiofrequency Current Adjacent to the Cervical Dorsal Root Ganglion of the Rat Induces Late Cellular Activity in the Dorsal Horn. Anesthesiology. 102 (1): 125-31.
Vaughan, R. 1975. Percutaneous Radiofrequency Gangliotomy in the Treatment of Trigeminal Neuralgia and Other Facial Pain. Aust. NZ. J. Surg. 45 (2): 203-7. (Abstract Only).
Viton, J.-M. et al. 1998. Short-Term Assessment of Periradicular Corticosteroid Injections in Lumbar Radiculopathy Associated With Disc Pathology. Neuroradiology. 40 (1): 59-62.
Viton, J. M. et al. 1998. Short-Term Evaluation of Periradicular Corticosteroid Injections in the Treatment of Lumbar Radiculopathy Associated With Disc Disease. Rev. Rhum. Engl. Ed. 65 (3): 195-200. (Abstract Only).
Wagner, A. L. et al. 2002. Selective Nerve Root Blocks. Tech. Vasc. Interv. Radiol. 5 (4): 194-200. (Abstract Only).
Waxman, S. G. et al. 1999, Sodium channels, excitability of primary sensory neurons, and the molecular basis of pain; Muscle Nerve; 22(9); pp. 1177-1187.
Weiner, R. L. 2000. The Future of Peripheral Nerve Neurostimulation. Neurological Research. 22 (3): 299-304.
Weiner, R. L. 2003. Peripheral Nerve Neurostimulation. Neurosurgery Clinics of North America. 14 (3): 401-408.
Weinstein, J. et al. 1988. The Pain of Discography. Spine. 13 (12):1344-8.
Wessels, W. J. et al. 1993. A rostrocaudal somatotopic organization in the brachial dorsal root ganglia of neonatal rats; Clin. Neural. Neurosurg; 95 Suppl; pp. S3-11.
Wessels, W. J. et al. 1990. Evidence for a rostrocaudal organization in dorsal root ganglia during development as demonstrated by intra-uterine WGA-HRP injections into the hindlimb of rat fetuses; Brain Res. Dev. Brain Res. 54(2); pp. 273-281.
Wessels et al.; Somatotopic organization in the sensory innervation of the rat hindlimb during development, using half dorsal root ganglia as subsegmental units; Eur. J. Morphol; 28(2-4); pp. 394-403; 1990.

(56) References Cited

OTHER PUBLICATIONS

Wessels, W. J. et al. 1994. The rostrocaudal organization in the dorsal root ganglia of the rat: a consequence of plexus formation?; Anat. Embryol. (Berl); 190 (1); pp. 1-11.
Wetzel, F. T. et al. 1997. Extradural Sensory Rhizotomy in the Management of Chronic Lumbar Radiculopathy: A Minimum 2-Year Follow-up Study. Spine. 22 (19): 2283-2291.
Wetzel, F. T. 1992. Chronic Benign Cervical Pain Syndromes: Surgical Considerations. Spine. 17 (10): S367-74. (Abstract Only).
Wetzel, F. T. et al. 1992. The Treatment of Chronic Extremity Pain in Failed Lumbar Surgery. The Role of Lumbar Sympathectomy. Spine. 17 (12): 2367-8. (Abstract Only).
White, P. F. et al. 2003. The Use of a Continue Popliteal Sciatic Nerve Block After Surgery Involving the Foot and Ankle: Does It Improve the Quality of Recovery? Anesth. Analg. 97 (5): 1303-9. (Abstract Only).
Whitworth, L. A. et al. 2002. Application of Spinal Ablative Techniques for the Treatment of Benign Chronic Painful Conditions. Spine. 27 (22): 2607-2612.
Wilkinson, H. A. et al. 2001. Sensory Ganglionectomy: Theory, Technical Aspects, and Clinical Experience. J. Neurosurg. 95 (1): 61-6. (Abstract Only).
Wong, C. B. et al. 2002. Clinical Outcomes of Revision Lumbar Spinal Surgery: 124 Patient With a Minimum of Two Years of Follow-Up. Chang Gung Med. J. 25 (3): 175-82. (Abstract Only).
Wright, R. E. et al. 1998. Neurostimulation of the L2 Dorsal Root Ganglion for Intractable Disc Pain: Description of a Novel Technique. Presented at the IFESS.
Wu, G. et al. 2001. Early Onset of Spontaneous Activity in Uninjured C-Fiber Nociceptors After Injury to Neighboring Nerve Fibers. Journal of Neuroscience. 21 (8): RC140.
Yamashita, T. et al. 2002. A Quantitative Analysis of Sensory Function in Lumbar Radiculopathy Using Current Perception Threshold Testing. Spine. 27 (14): 1567-1570.
Yoshida, H. et al. 1997. Lumbar Nerve Root Compression Caused by Lumbar Intraspinal Gas: Report of Three Cases. Spine. 22 (3): 348-351.
Young, R. F. 1996. Chapter 161: Dorsal Rhizotomy and Dorsal Root Ganglionectomy (pp. 3442-3451). 176 Neurological Surgery 4th Edition. (Julian R. Youmans ed.). Philadelphia: W. B. Saunders Company.
Burdulis, A. G.; U.S. Appl. No. 13/175,488 entitled "Hard tissue anchors and delivery devices," filed Jul. 1, 2011.

\* cited by examiner

METHODS, SYSTEMS AND DEVICES FOR REDUCING MIGRATION

CROSS-REFERENCES TO RELATED APPLICATIONS

This application is a continuation of U.S. patent application Ser. No. 15/178,012, entitled "Methods, Systems and Devices for Reducing Migration," filed Jun. 9, 2016, U.S. Pat. No. 10,456,576 which is a continuation of U.S. patent application Ser. No. 13/104,787, entitled "Methods, Systems and Devices for Anchoring in the Epidural Space," filed May 10, 2011, which claims priority under 35 U.S.C. 119(e) to U.S. Provisional Patent Application Ser. No. 61/333,199, entitled "Methods, Systems and Devices for Anchoring in the Epidural Space," filed May 10, 2010, which are incorporated herein by reference.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND

Neuromodulation is a method of treating pain symptoms by therapeutically altering activity in pain pathways with the use of an implantable device. Neuromodulation works by either actively stimulating nerves with electrical energy to produce a natural biological response or by applying targeted pharmaceutical agents in small doses directly to a site of action.

Electrical stimulation involves the application of electrodes to the brain, the spinal cord or peripheral nerves of a patient. These precisely placed electrodes are typically mounted on a lead that is connected to a pulse generator and power source, which generates the necessary electrical stimulation. A low-voltage electrical current passes from the generator to the nerve, and can either inhibit pain signals or stimulate neural impulses where they were previously absent. One of the most common types of electrical stimulation is spinal cord stimulation (SCS), which has been used as a treatment option for patients with chronic pain since the 1960s. In the last 30 years, it has become a standard treatment for patients with chronic pain in their back and/or limbs who have not found pain relief from other treatments. While the treatment does not work for everyone, many patients who qualify for neurostimulation therapy receive a reduction in overall pain. Some patients find that they can decrease their pain medication after undergoing spinal cord stimulation. Given these benefits, many individuals suffering from chronic pain find that neurostimulation positively impacts the quality of their lives.

In some instances, neuromodulation can alternatively been achieved by delivering pharmacological agents through implanted leads or catheters. In this manner, the agent can be administered in smaller doses because it does not have to be metabolized and pass through the body before reaching the target area. Smaller doses—in the range of 1/300 of an oral dose—can mean fewer side effects, increased patient comfort and improved quality of life.

However, neuromodulation is not without its risks and complications. One complication associated with the implantation of leads is lead migration which can cause loss of effective stimulation over time. During migration, the stimulation electrodes, typically at the distal end of the lead, move in relation to the nerve creating a less desirable stimulation effect. Traditional SCS leads are positioned within the epidural space which is a largely unconfined area. In addition, such leads are typically anchored outside of the epidural space, such as to the fascia above the supraspinous ligament or to the supraspinous ligament itself. Consequently, the portion of the lead distal to the anchor is free to move along the entire length of the lead from the point of anchor to the tip in any direction within the epidural space. Such movement can reposition the lead such that stimulation is altered or even negated over time. Similarly, catheters positioned within the epidural space can also suffer from migration leading to agents being delivered outside of the target location.

Movement or migration of the lead can be caused by: 1) body motions (flexion, torsion, and so on); 2) tensile force transferred to the distal end of the lead from the proximal portion of the lead (i.e. from the anchor IPG connection point, or fascia, or ligaments); 3) gravity settling of the lead body; and/or 4) other factors. An anchor or other means to prevent migration is intended to prevent or reduce motion of the distal end of the lead due to these causes.

Improved anchoring of leads and catheters are desired. Such anchoring should be noninvasive to avoid damaging or harming the patient anatomy, particularly delicate nerve tissue and, in some instances, reversible so as to allow a revision of the system without having to access the epidural space directly to remove the lead. At least some of these objectives will be met by the present invention.

BRIEF SUMMARY

The present invention provides devices, systems and methods for reducing migration of leads, catheters and similar devices. In particular, devices, systems and methods are provided for creating a slack anchor which assists in maintaining the lead or catheter in a desired position. In some embodiments, the slack anchor is created within the epidural space. When targeting nerve anatomy within the spinal column or in the vicinity of the epidural space, anchoring within the epidural space allows the associated lead or catheter to be anchored as close to the target therapy site as desired or possible. By anchoring close to the target therapy site, the risk of movement or migration is significantly reduced or eliminated.

The devices, systems and methods described herein are typically used in the treatment of pain. Treatment typically includes electrical stimulation and/or delivery of pharmacological or other agents to a target nerve site with the use of a lead or catheter. Examples herein will be described with the use of a lead providing electrical stimulation to a dorsal root or dorsal root ganglion (DRG) in the treatment of pain for illustration purposes. However, it may be appreciated that the present invention may be used in the treatment of other conditions, such as itching, Parkinson's Disease, Multiple Sclerosis, demylenating movement disorders, spinal cord injury, asthma, chronic heart failure, obesity and stroke (particularly acute ischemia), peripheral vascular disease, or angina pectoris, to name a few. Likewise, the present invention may be used to anchor devices targeting other therapy sites, such as the spinal cord itself, the dorsal root entry zone (DREZ), any sites which are accessible through the epidural space and/or any sites which allow creation of a slack anchor within the epidural space. Further, the present invention may be used to anchor devices targeting peripheral nerves. In such embodiments, the device such as a lead or catheter may not pass through the epidural space and the slack anchor may be formed within the body near the target peripheral nerve. Further, the present invention may be used to anchor any device having characteristics which allow the creation of a slack anchor.

In a first aspect of the present invention, a method of creating a slack anchor is provided. In some embodiments, the method includes positioning a lead having a distal end and a shaft so that the distal end is positioned at a target location and the shaft extends along a first path, advancing a sheath having a curved distal end over the shaft, manipulating the sheath so that the curved distal end directs a portion of the shaft lateral to the first path and advancing the lead beyond the curved distal end directing the portion of the shaft lateral to the first path so that the portion of the shaft resides along a second path forming the slack anchor while substantially maintaining position of the distal end at the target location. In some embodiments, the slack anchor is formed within an epidural space.

In some embodiments, the second path has a serpentine shape. In other embodiments, the second path has a loop shape. It may be appreciated that in some embodiments, the target location comprises a dorsal root ganglion. In such embodiments, the slack anchor may be formed at a location within the spinal column near the dorsal root ganglion. However, the lead may be positioned to target other anatomies and the slack anchor may be formed at other locations.

In some embodiments, the slack anchor creates sufficient friction to resist migration of the distal end in relation to the target location. In other embodiments, migration movement of the shaft is at least partially absorbed by the slack anchor to resist migration of the distal end in relation to the target location.

In a second aspect of the present invention, a method is provided of positioning a lead within an epidural space. In some embodiments, the method comprises advancing a distal end of the lead from an entry point into the epidural space to a target location so that a portion of a shaft of the lead extends from the entry point to the target location along a first path within the epidural space, and introducing an additional portion of the shaft of the lead into the epidural space in a manner that forms a slack anchor between the target location and the entry point.

In some embodiments, the slack anchor creates sufficient friction to resist migration of the distal end in relation to the target location. In other embodiments, migration movement of the shaft is at least partially absorbed by the slack anchor to resist migration of the distal end in relation to the target location.

In some embodiments, introducing the additional portion comprises positioning the additional portion of the shaft of the lead along a second path, wherein at least part of the second path is lateral to the first path. It may be appreciated that in some instances the slack anchor has a serpentine shape and in other instances the slack anchor has a loop shape. In some embodiments, the shaft includes a kink point so that introducing the additional portion of the shaft causes the shaft to bend near the kink point which assists in creating the slack anchor.

In some embodiments, the method of positioning a lead within an epidural space further comprises advancing a sheath having a curved distal end over the portion of the shaft so that the curved distal end directs the introduction of the additional portion. Optionally, the method further comprises manipulating the curved distal end to direct the introduction of the additional portion in a direction that is substantially lateral to the first path. In some instances, the target location comprises a dorsal root ganglion. In such instances, the slack anchor may be formed at a location within the spinal column near the dorsal root ganglion.

In a third aspect of the present invention, a device for treating a target location is provided. In some embodiments, the device comprises a lead comprising a shaft having at least one electrode disposed along its distal end and a structural kink point disposed along the shaft proximal to the at least one electrode so that the structural kink point resides within an epidural space while the at least one electrode is positioned near the target location, wherein the structural kink point assists in creating a slack anchor when a portion of the shaft is advanced into the epidural space while the position of the at least one electrode is substantially maintained near the target location.

In some embodiments, the structural kink point comprises a change in material stiffness. In such embodiments, the structural kink point may comprise a flexible region disposed distally to a more rigid region. For example, the shaft may be comprised of at least one tube and the more rigid region may be formed by potting of the at least one tube.

In some embodiments, the distal end of the lead is configured for positioning the at least one electrode near a dorsal root ganglion. Optionally, the structural kink point may be disposed so as to create the slack anchor adjacent to a dorsal root associated with the dorsal root ganglion. In some embodiments, the slack anchor has a serpentine shape. In other embodiments, the slack anchor has a loop shape.

Other objects and advantages of the present invention will become apparent from the detailed description to follow, together with the accompanying drawings.

DETAILED DESCRIPTION

Figure 1:
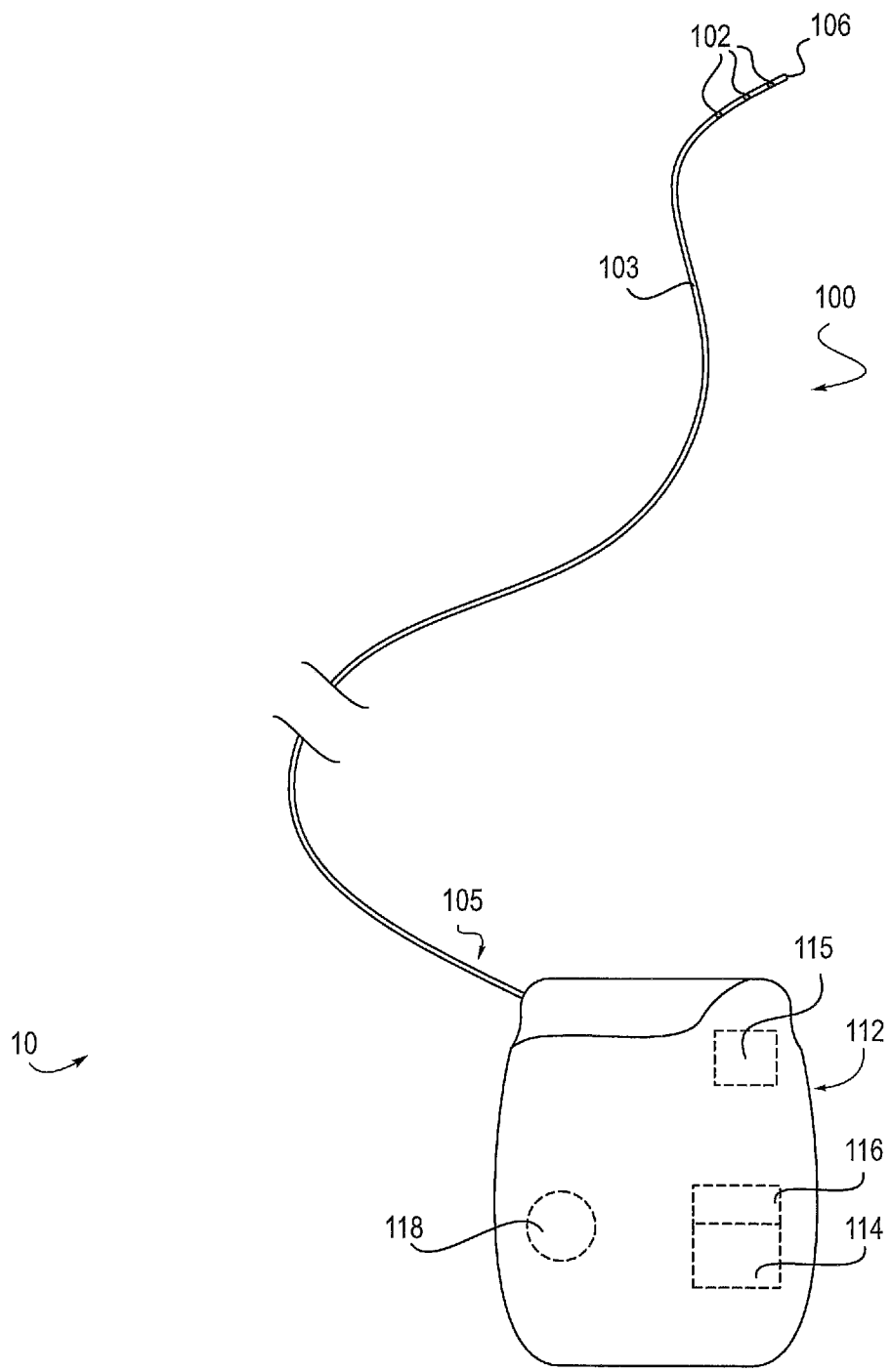
FIG. 1 illustrates an example stimulation system which may utilize a slack anchor.

FIG. 1 illustrates an example stimulation system 10 which may utilize a slack anchor for anchoring the lead 100, such as within the epidural space of a patient. In this embodiment, the stimulation system 10 includes a lead 100, having at least one electrode 102 disposed thereon, and an implantable pulse generator (IPG) 112. The lead 100 comprises a shaft 103 having a proximal end 105 and a distal tip 106. The proximal end 105 is insertable into the IPG 112 to provide electrical connection to the lead 100. The IPG 112 contains a processor 114, an antenna 115, programmable stimulation information in memory 116, as well as a power supply 118, e.g., a battery, so that once programmed and turned on, the IPG 112 can operate independently of external hardware. The IPG 112 is turned on and off and programmed to generate the desired stimulation pulses from an external programming device using transcutaneous electromagnetic or RF links. The stimulation information includes signal parameters such as voltage, current, pulse width, repetition rate, and burst rates. Example stimulation information is provided in U.S. patent application Ser. No. 12/607,009 entitled "Selective Stimulation Systems and Signal Parameters For Medical Conditions", filed Oct. 27, 2009, incorporated herein by reference for all purposes.

Figures 2A, 2B, 2C, 2D:
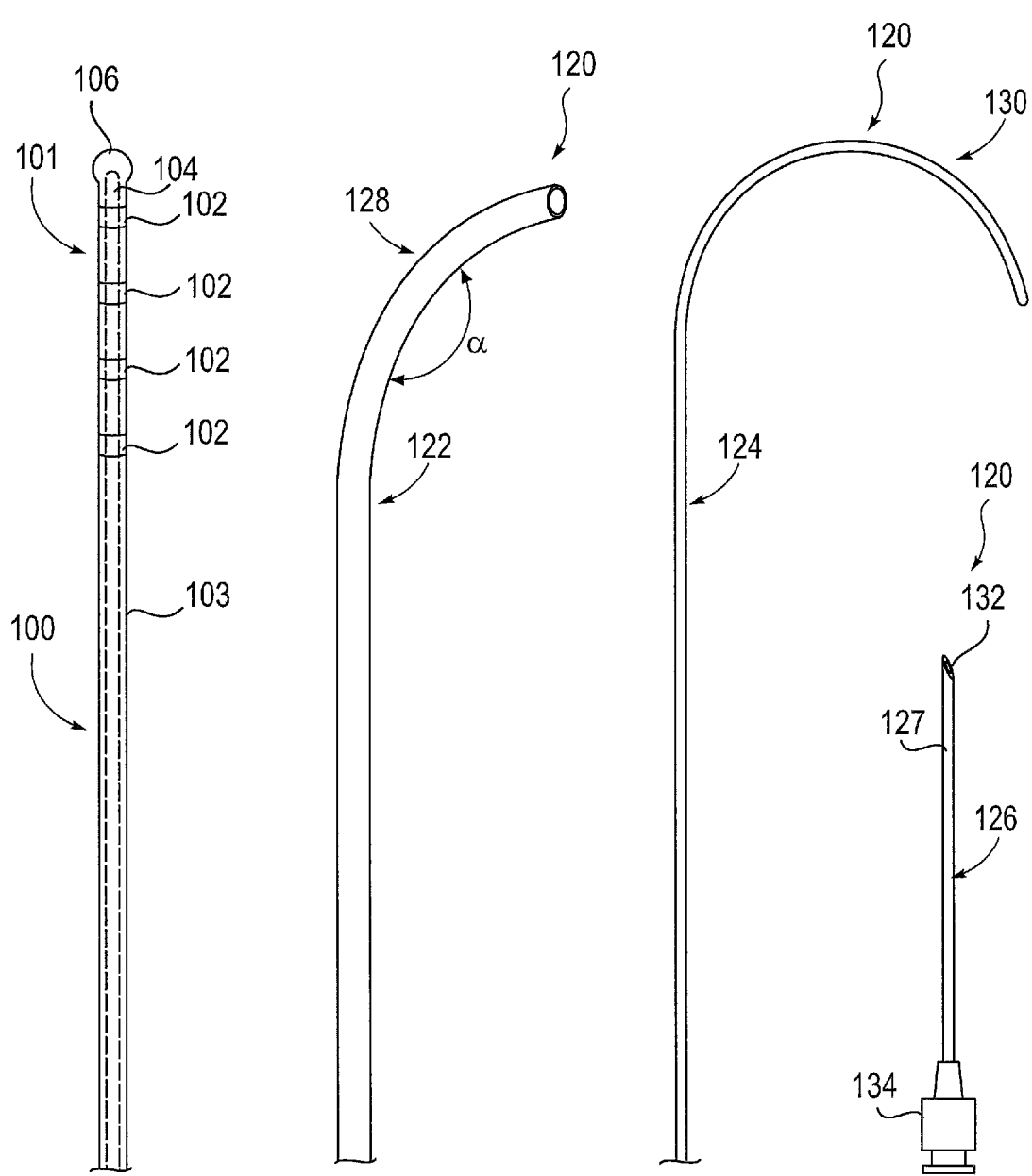
FIGS. 2A-2D illustrate an example lead and delivery devices for accessing a target site and creating a slack anchor.

Desired positioning of the lead 100 near a target site, such as the DRG, and creation of the slack anchor may be achieved with a variety of delivery systems, devices and methods. Referring to FIGS. 2A-2D, an example lead and delivery devices for accessing a target site and creating a slack anchor are illustrated. FIG. 2A illustrates an embodiment of a lead 100 comprising a shaft 103 having a distal end 101 with four electrodes 102 disposed thereon. It may be appreciated that any number of electrodes 102 may be present, including one, two, three, four, five, six, seven, eight or more. In this embodiment, the distal end 101 has a closed-end distal tip 106. The distal tip 106 may have a variety of shapes including a rounded shape, such as a ball shape (shown) or tear drop shape, and a cone shape, and donut shape to name a few. These shapes provide an atraumatic tip for the lead 100 as well as serving other purposes. The lead 100 also includes a stylet lumen 104 which extends toward the closed-end distal tip 106. A delivery system 120 is also illustrated, including a sheath 122 (FIG. 2B), stylet 124 (FIG. 2C) and introducing needle 126 (FIG. 2D).

Figures 3, 4:
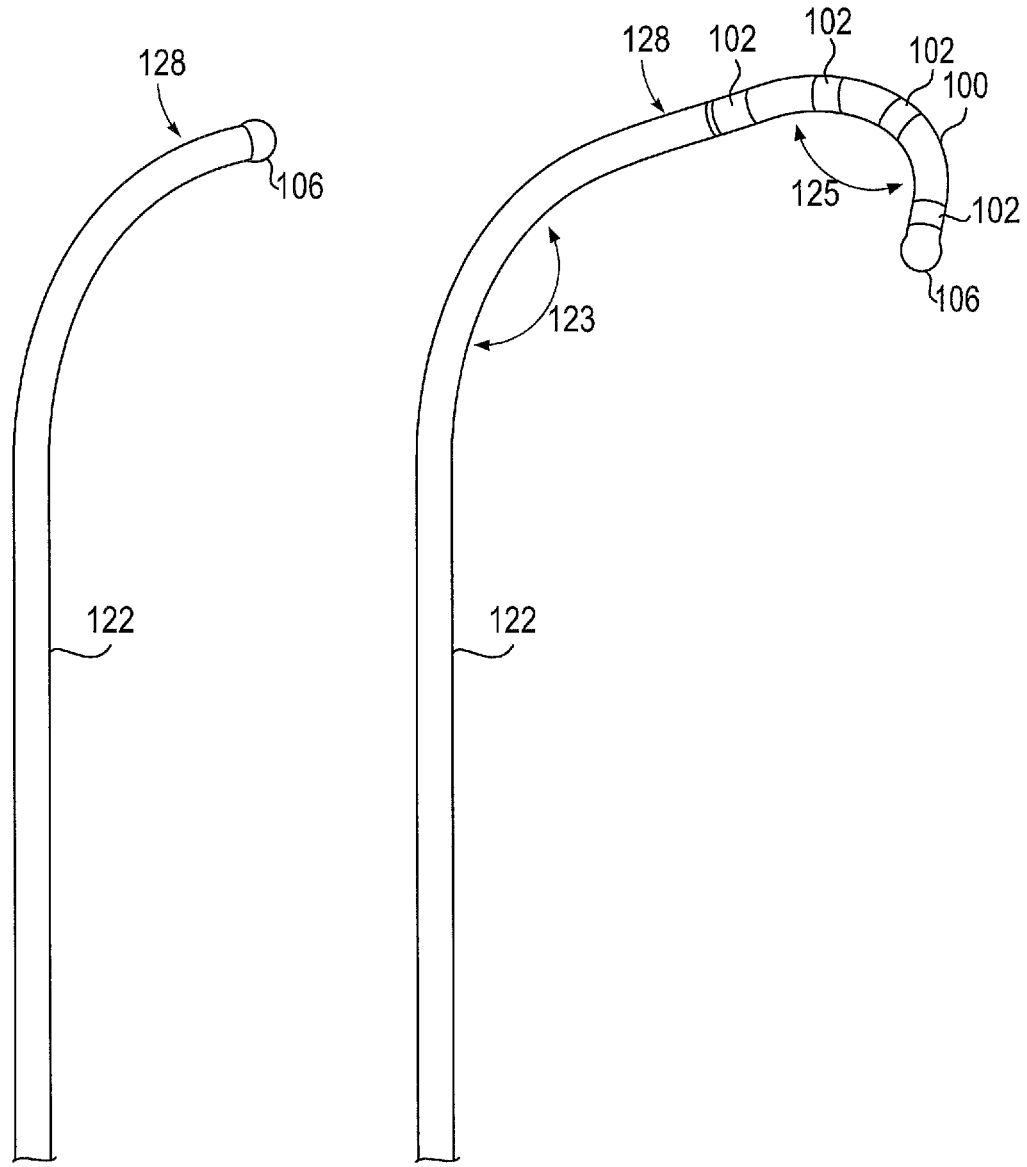
FIG. 3 illustrates an embodiment of a sheath advanced over a shaft of a lead with an internal stylet forming a first curvature.
FIG. 4 illustrates the lead with the internal stylet of FIG. 3 extending beyond the sheath forming a second curvature.

Referring to FIG. 2B, an embodiment of a sheath 122 is illustrated. In this embodiment, the sheath 122 has a distal end 128 which is pre-curved to have an angle .alpha. In some embodiments, the angle .alpha. is in the range of approximately 80 to 165 degrees. The sheath 122 is sized and configured to be advanced over the shaft 103 of the lead 100 until a portion of its distal end 128 abuts the distal tip 106 of the lead 100, as illustrated in FIG. 3. Thus, the ball shaped tip 106 of this embodiment also prevents the sheath 122 from extending thereover. Passage of the sheath 122 over the lead 100 causes the lead 100 to bend in accordance with the precurvature of the sheath 122. Thus, when approaching a target DRG, the sheath 122 assists in steering the lead 100 along the spinal cord S and toward the target DRG, such as in a lateral direction.

Referring back to FIG. 20, an embodiment of a stylet 124 is illustrated. The stylet 124 has a distal end 130 which is pre-curved. In some embodiments, the precurvature has a radius of curvature is in the range of approximately 0.1 to 0.5. The stylet 124 is sized and configured to be advanced within the stylet lumen 104 of the lead 100. Typically the stylet 124 extends therethrough so that its distal end 130 aligns with the distal end 101 of the lead 100. Passage of the stylet 124 through the lead 100 causes the lead 100 to bend in accordance with the precurvature of the stylet 124. Typically, the sty/et 124 has a smaller radius of curvature, or a tighter bend, than the sheath 122. Therefore, as shown in FIG. 4, when the stylet 124 is disposed within the lead 100, extension of the lead 100 and stylet 124 through the sheath 122 bends or directs the lead 100 through a first curvature 123. Further extension of the lead 100 and stylet 124 beyond the distal end 128 of the sheath 122 allows the lead 100 to bend further along a second curvature 125. When approaching a target DRG, this allows the laterally directed lead 100 to now curve around toward the target OR along the nerve root. This two step curvature allows the lead 100 to be successfully positioned so that at least one of the electrodes 102 is on, near or about the target DRG, particularly by making a sharp turn along the nerve root.

Thus, the lead 100 does not require stiff or torqueable construction since the lead 100 is not torqued or steered by itself. The lead 100 is positioned with the use of the sheath 122 and stylet 124 which direct the lead 100 through the two step curvature. This eliminates the need for the operator to torque the lead 100 itself and allows the lead 100 to have a lower profile as well as a very soft and flexible construction. This, in turn, minimizes erosion and discomfort created by pressure on nerve tissue, such as the target DRG and/or the nerve root, once the lead 100 is implanted. For example, such a soft and flexible lead 100 will minimize the amount of force translated to the tip of the lead 100 by body movement (e.g. flexion, extension, torsion) which in turn will reduce the variability in position of the lead with respect to the target tissue.

Referring back to FIG. 2D, an embodiment of an introducing needle 126 is illustrated. The introducing needle 126 is used to access the epidural space of the spinal cord S. The needle 126 has a hollow shaft 127 and typically has a very slightly curved distal end 132. The shaft 127 is sized to allow passage of the lead 100, sheath 122 and stylet 124 therethrough. In some embodiments, the needle 126 is 14 gauge which is consistent with the size of epidural needles used to place conventional percutaneous leads within the epidural space. However, it may be appreciated that other sized needles may also be used, particularly smaller needles such as 16-18 gauge. Likewise, it may be appreciated that needles having various tips known to practitioners or custom tips designed for specific applications may also be used. The needle 126 also typically includes a Luer-Lok™ fitting 134 or other fitting near its proximal end. The Luer-Lok™ fitting 134 is a female fitting having a tabbed hub which engages threads in a sleeve on a male fitting, such as a syringe.

In some embodiments, the above described lead 100 and delivery system 120 is used to create a slack anchor. FIGS. 5A-5D illustrate an embodiment of a method of creating a slack anchor with the use of a lead 100 and delivery system 120 described above. In this embodiment, the lead 100 is delivered to a DRG from an antegrade approach. Each DRG is disposed along a dorsal root DR and typically resides at least partially between the pedicles PD or within a foramen. Each dorsal root DR exits the spinal cord S at an angle .theta. This angle .theta. is considered the nerve root sleeve angulation and varies slightly by patient and by location along the spinal cord. In many instances, the nerve root angulation is significantly less than 90 degrees and sometimes less than 45 degrees. Therefore, advancement of the lead 100 toward the target DRG in this manner involves making a sharp turn along the angle .theta. Turns of this severity are achieved with the use of the delivery system 120.

Figure 5A:
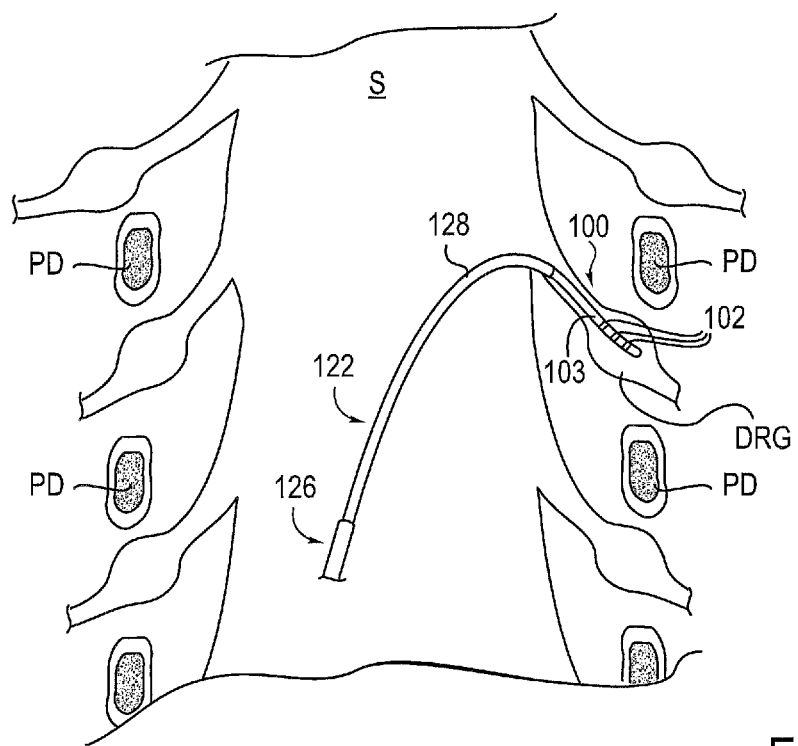
FIGS. 5A-5D illustrate an embodiment of a method of creating a slack anchor.

In this embodiment, the epidural space is accessed with the use of the introducing needle 126. Once the needle 126 has been successfully inserted into the epidural space, the lead 100 is delivered to the target DRG, as illustrated in FIG. 5A. The stylet 124 is inserted into the lead 100 and the sheath 122 is advanced over the lead 100. The sheath 122 is positioned so that its distal end 128 is near or against the distal tip 106 of the lead 100 causing the lead 100 to follow the curvature of the distal end of sheath 122. The assembled sheath 122/lead 100/stylet 124 is advanced within the epidural space toward a target DRG with the precurvature of the sheath 122 directing the lead 100 laterally outwardly. The lead 100/stylet 124 is then advanced beyond the distal end 128 of the sheath 122. The curvature of the stylet 124 within the lead 100 causes the lead 100 to bend further, along this curvature. This allows the laterally directed lead 100 to now curve around toward the target DRG along the nerve root angulation. This two step curvature allows the lead 100 to be successfully steered to position at least one of the electrodes 102 on, near or about the target DRG. Such methods of deliver are further described and illustrated in U.S. patent application Ser. No. 12/687,737, entitled "Stimulation Leads, Delivery Systems and Methods of Use", filed Jan. 14, 2010; incorporated herein by reference for all purposes, along with examples of other delivery systems, devices and methods applicable to use with the present invention.

Figure 5B:
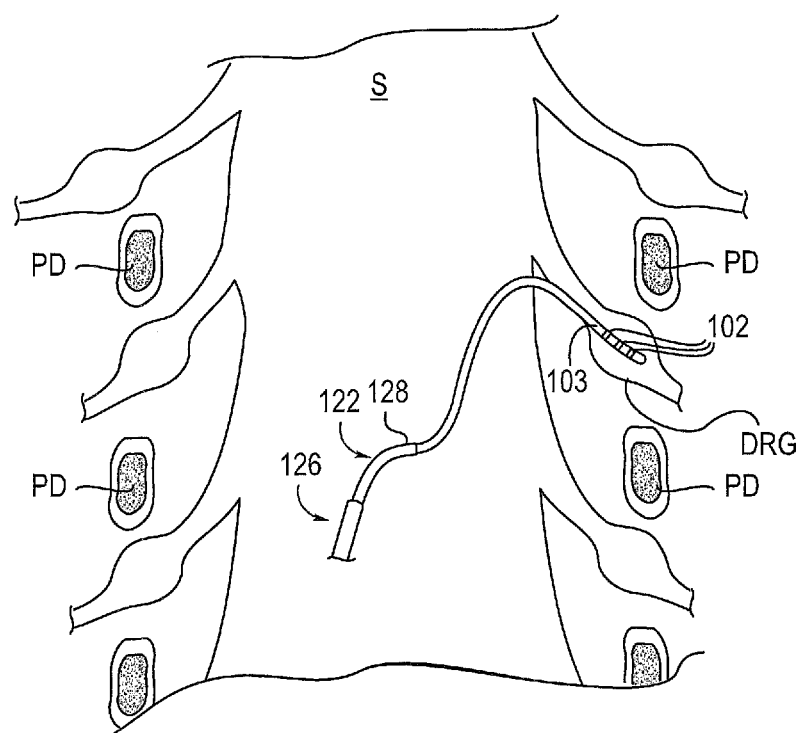

Thus, distal end 101 of the lead 100 is positioned at the target location and the shaft 103 extends along a first path. The sheath 122 and stylet 124 are then retracted, leaving the flexible shaft 103 of the lead 100 extending along the first path Referring to FIG. 5B, the sheath 122 is manipulated so that the curved distal end 128 directs a portion of the shaft 103 lateral to the first path within the epidural space. FIG. 5B shows the sheath 122 directing a portion of the shaft 103 laterally outward, away from the midline of the spinal cord S. However it may be appreciated that the sheath 122 may be rotated so as to direct a portion of the shaft 103 laterally inward, toward the midline of the spinal cord S. Likewise, the sheath 122 may be manipulated so as to face a variety of other directions.

Figure 5C:
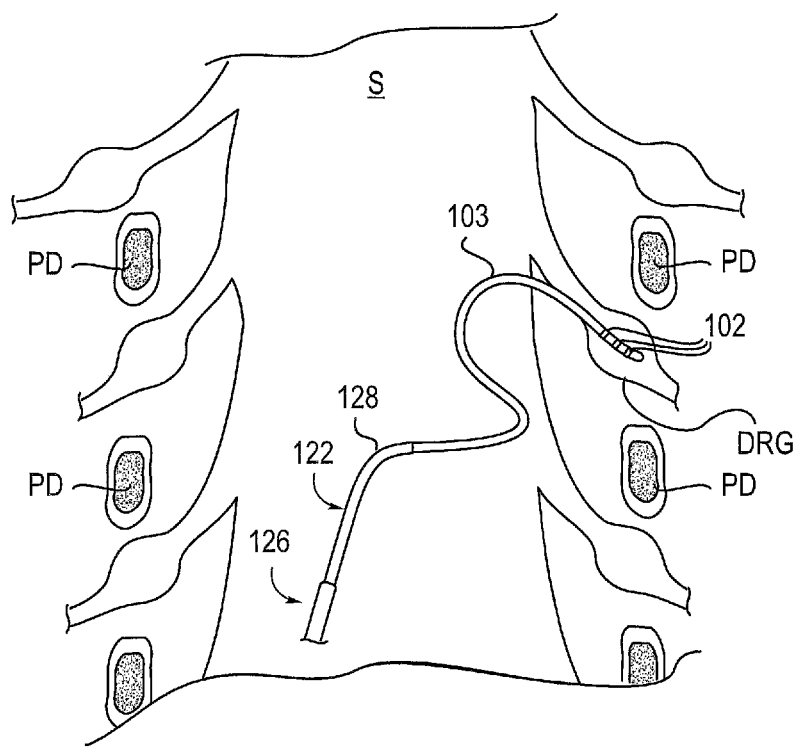

Referring to FIG. 5C, the lead 100 is then advanced beyond the curved distal end 128 of the sheath 122. Since the stylet 124 has been retracted, the shaft 103 of the lead 100 is very flexible, particularly in contrast to the sheath 122. The more rigid distal end 128 of the sheath 122 directs a portion of the flexible shaft 103 lateral to the first path so that this portion of the flexible shaft 103 resides along a second path. Thus, the difference in stiffness or flexibility between the sheath 122 and the shaft 103 of the lead 100 creates a "kink point" or bend area allowing the shaft 103 to bend and curve. This portion of curved lead 100 forms the slack anchor. Thus, the curvatures of the lead 100 provide slack and/or anchoring. The slack absorbs any movement or migration of the lead 100 within the epidural space and prevents or minimizes translation such movement to the distal end 101. This allows the distal end 101 to maintain its position and continue to provide desired stimulation to the target site. The anchoring is achieved by frictional forces created by the curvatures of the lead 100 within the epidural space and the increased surface area created by the slack. The slack and anchoring significantly reduces or eliminates the risk of migration of the leads within the epidural space.

It may be appreciated that the slack anchor may alternatively or additionally be formed with the use of the stylet 124. In such embodiments, the stylet 124 is advanced beyond the distal end 128 of the sheath 122 to a desired location within the shaft 103 of the lead 100. The stylet 124 provides increased rigidity to the shaft 103 along the areas where the stylet 124 resides within. Thus, the location where the stylet 124 ends within the shaft 103 creates a natural kink point allowing the shaft 103 to bend and curve. Consequently, the stylet 124 can be manipulated to create a variety of curvatures at any desired location along the shaft 103 of the lead 100.

In conventional spinal cord stimulation, the SCS lead is either delivered without a delivery sheath or the lead is delivered with the use of a delivery sheath which does not impart stiffness. Likewise, the lead itself is of consistent stiffness. Without a means for creating difference in stiffness, a kink point cannot be created and therefore a slack anchor cannot be easily formed.

Figure 5D:
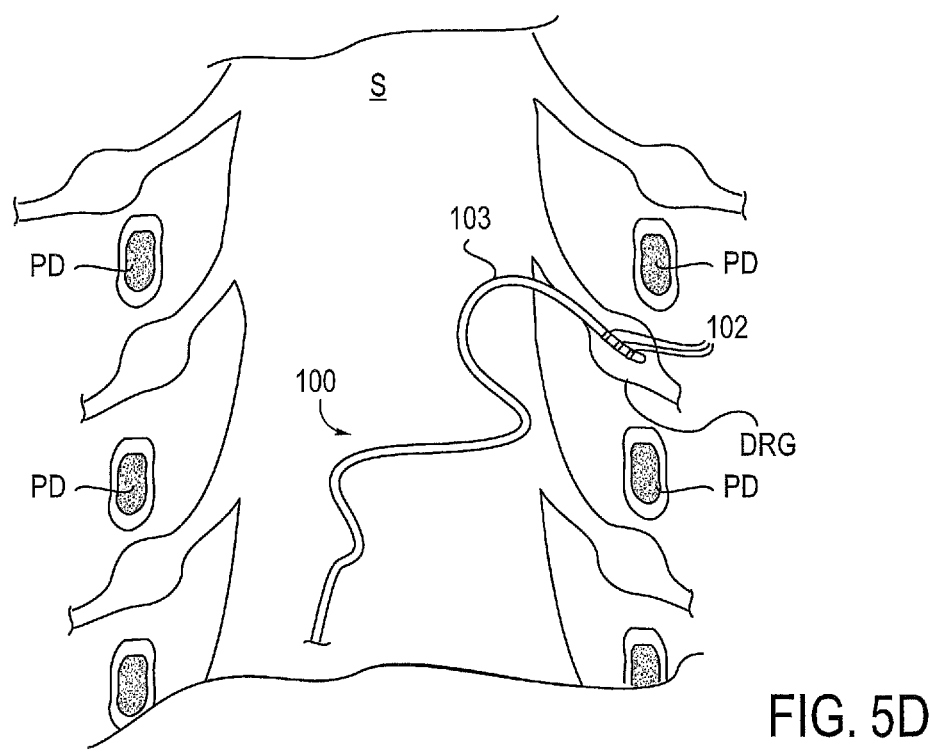

In the present invention, a variety of different slack anchors may be formed by manipulating the sheath 122 and/or stylet 124. Once the desired slack anchor is created, the sheath 122 and stylet 124 are removed and the lead 100 is left in place, as illustrated in FIG. 5D. Since the slack anchor is disposed within the epidural space, the lead 100 is anchored as close to the target therapy site, such as the DRG, as possible. In this example, the slack anchor is formed at a location along the spinal cord, adjacent the dorsal root. By anchoring close to the target therapy site, the risk of movement or migration of the distal end 102 of the lead 100 is significantly reduced or eliminated. Such anchoring is particularly useful when accessing the epidural space on the same spinal level as the target therapy site or on a spinal level which is adjacent or nearby the target therapy site. In such instances, the distance between the entry site and the target therapy site is relatively short which increases the risk of migration. Thus, the use of a slack anchor is particularly useful in resisting migration in these instances.

Figure 6:
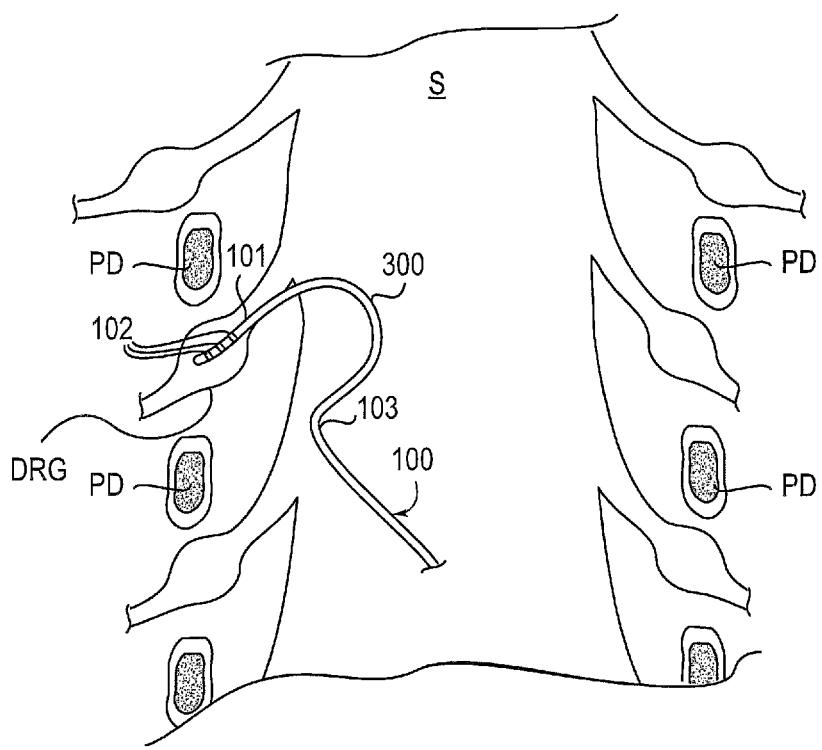
FIG. 6 illustrates an embodiment of a slack anchor having a serpentine shape comprising a single switchback.
Figure 7:
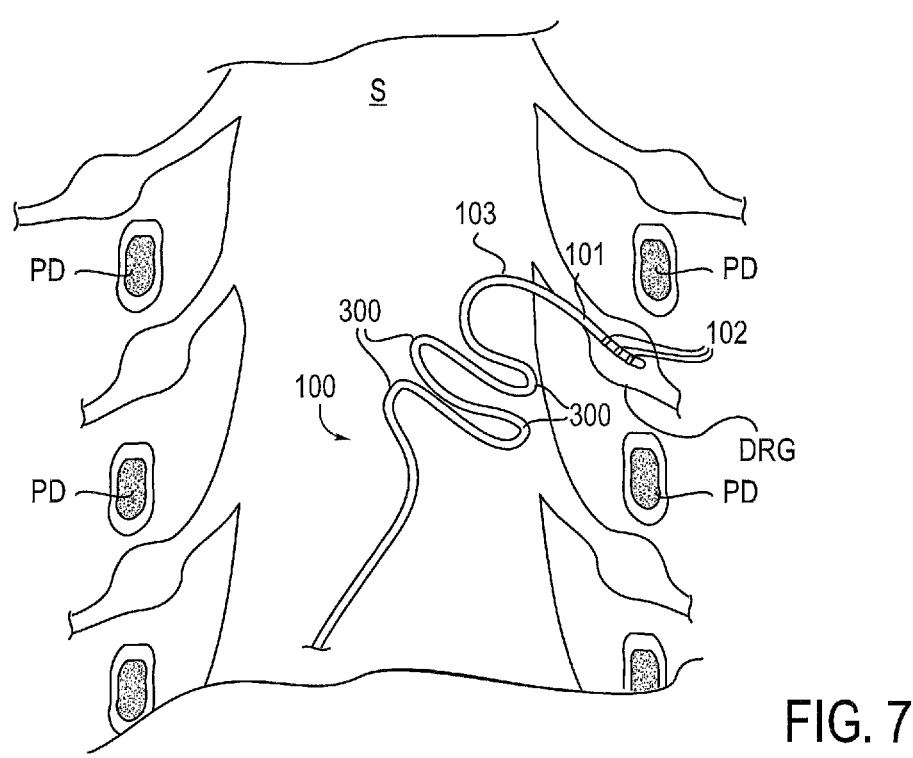
FIG. 7 illustrates an embodiment of a slack anchor having a serpentine shape comprising a plurality of switchbacks.

The slack anchors of the present invention may have a variety of shapes or forms. In some embodiments, the slack anchor has a serpentine shape. In such embodiments, the shaft 103 of the lead 100 curves through one or more switchbacks, such as forming an S shape, snake shape, or zigzag shape. The switchbacks may be short, such as to form wavy shapes, or long, such as to form lobe shapes. In addition, the number of switchbacks may be minimal, such as one or two, or more plentiful. FIG. 6 illustrates an embodiment of a slack anchor having a serpentine shape comprising a single switchback 300. Here, the distal end 101 of the lead 100 is positioned near a DRG and the shaft 101 extends along the nerve root angulation and along portions of the spinal cord. Had the lead 100 not included a slack anchor, the shaft 103 would reside along a first path extending toward the point of entry to the epidural space. However, in this embodiment, the shaft 103 is positioned along a second path having the serpentine shape which forms the slack anchor. FIG. 7 illustrates an embodiment of a slack anchor having a serpentine shape comprising a plurality of switchbacks 300. In this embodiment, four switchbacks 300 are present. Each switchback 300 is relatively long so as to form lobe shapes.

Figure 8:
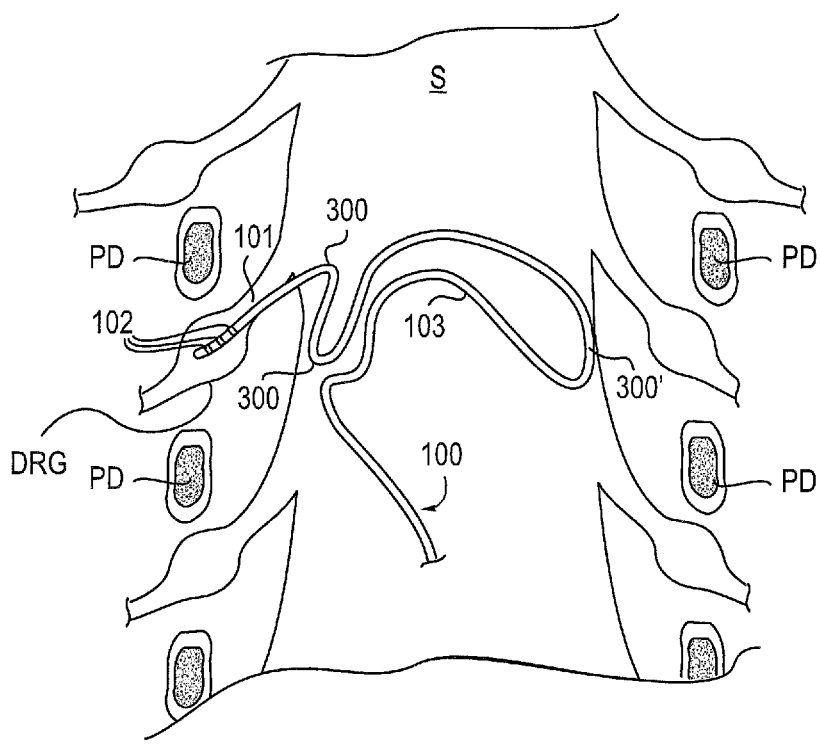
FIG. 8 illustrates an embodiment of a slack anchor having an irregular shape.

In some embodiments, the slack anchor has an irregular shape, such as a combination of shapes. For example, FIG. 8 illustrates an embodiment of a slack anchor having an irregular shape. Here, the distal end 101 of the lead 100 is positioned near a DRG and the shaft 101 extends along the nerve root angulation into the spinal area of the spinal cord S. Again, had the lead 100 not included a slack anchor, the shaft 103 would reside along a first path extending toward the point of entry to the epidural space. However, in this embodiment, the shaft 103 is positioned along a second path having the irregular shape which forms the slack anchor. The second path includes a serpentine shape, wherein the shaft 103 extends through two small switchbacks 300. The second path then extends across the epidural space forming a large switchback or lobe 300' before extending toward the point of entry. In this embodiment, the slack anchor extends across the width of the spinal cord S providing significant slack and anchoring capabilities.

Figure 9:
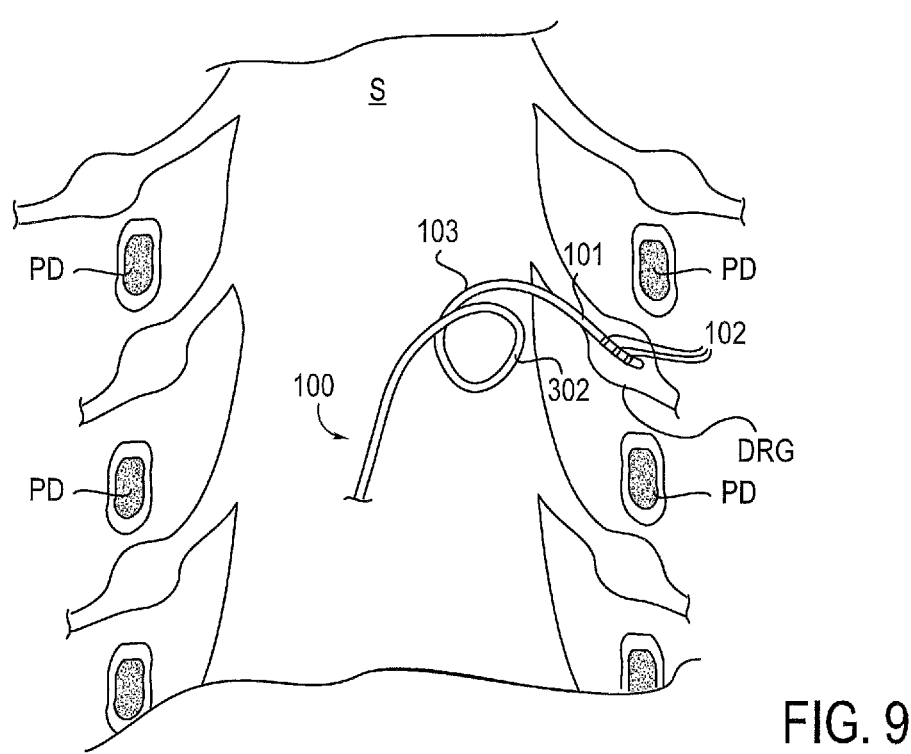
FIG. 9 illustrates an embodiment of a slack anchor having a loop shape.

In some embodiments, the slack anchor has a loop shape. For example, FIG. 9 illustrates an embodiment of a slack anchor having a loop shape. Here, the loop shape is formed by creating a switchback that crosses over itself forming a loop 302. As shown in FIG. 9, the distal end 101 of the lead 100 is positioned near a DRG and the shaft 101 extends along the nerve root angulation into the spinal column. The shaft 101 begins along a first path and then extends along a second path having a loop shape. In this embodiment, the loop 302 extends away from the midline of the spinal cord S. However, it may be appreciated that in some embodiments the loop 302 extends toward the midline of the spinal column S. Likewise, it may be appreciated that any number of loops 302 may be present and the loops 302 may be of any size.

Figure 10:
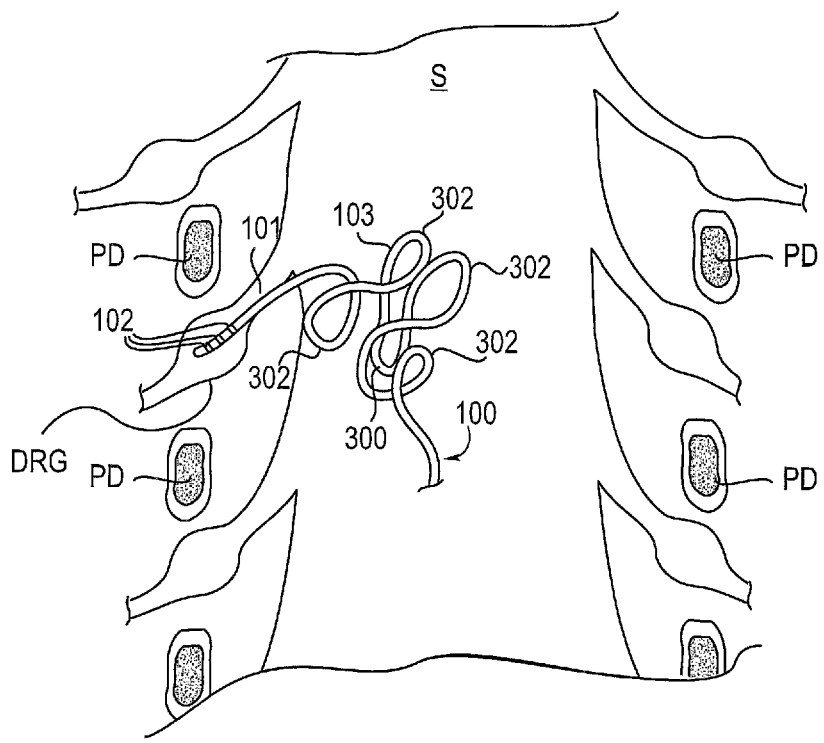
FIG. 10 illustrates an embodiment of a slack anchor comprised of a variety of serpentine and loop shapes.

In some embodiments, the slack anchor has a combination of serpentine and loop shapes. For example, FIG. 10 illustrates an embodiment of a slack anchor comprised of a variety of serpentine and loop shapes. In this embodiment, the slack anchor includes as least four loops 302, wherein some of the loops 302 cross over underlying switchbacks 300. Thus, the shaft 103 of the lead 100 follows a complex path forming the slack anchor.

In some embodiments, the slack anchor is configured to allow atraumatic removal of the lead 100 from the epidural space after the slack anchor has been formed. The epidural space is comprised of fluid and fibrous connective tissue. Fibrous tissue forms around the lead 100 over time creating a biological structure within the epidural space. The path of the lead 100 is essentially a tunnel or passageway through the biological structure so the lead 100 is able to move freely, and therefore migrate. However, the slack anchors of the present invention are supported by the biological structure so that the tunnels or passageways follow the curves and contours of the slack anchor path. Since the slack anchor path is non-linear, such as serpentine, the lead 100 is held in place by the biological structure and migration is reduced. In addition, if it is desired to remove the lead 100, the lead 100 may be withdrawn from the epidural space by gently pulling the proximal end of the lead 100 until the lead 100 is removed. The lead 100 will move through the tunnels or passageways, following the curves and contours of the slack anchor path. Such movement may be achieved with the force of withdrawal, however such movement is not achieved with the mere forces of migration. It may be appreciated that in some embodiments the slack anchor is configured to remain as a permanent anchor wherein the lead 100 is not easily removable after the biological structure has formed therearound. Such slack anchors are typically convoluted or complex resisting easy withdrawal of the lead 100 through the path.

Figure 11:
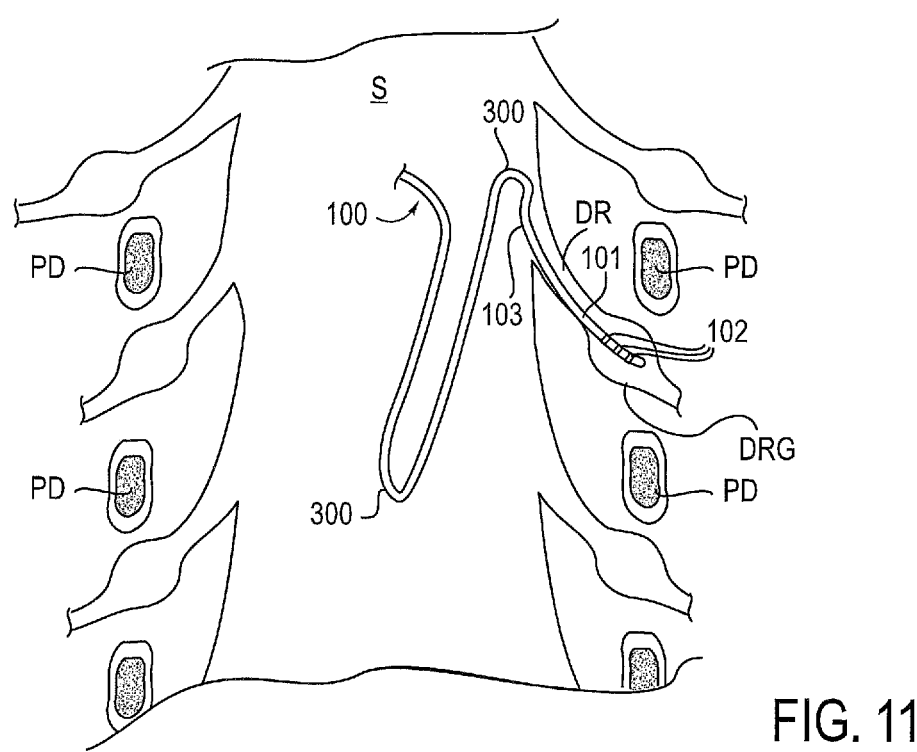
FIG. 11 illustrates an embodiment of a lead having a slack anchor which has been positioned with a retrograde approach.

It may be appreciated that although the epidural delivery methods described above illustrate an antegrade approach to a target site accessible through the epidural space, a variety of other approaches may also be used. For example, a retrograde, contralateral or transforaminal approach may be used, to name a few, FIG. 11 illustrates an embodiment of a lead 100 which has been positioned with a retrograde approach. Here the target site is the DRG and the lead 100 is positioned so that the at least one electrode is in the vicinity of the DRG. Thus, the distal end 101 of the lead 100 extends along the dorsal root DR and into the area of the spinal cord S where a slack anchor is formed by the shaft 103 of the lead 100. In this embodiment, the slack anchor is comprised of two switchbacks 300. Leads 100 positioned with this approach benefit greatly from the presence of a slack anchor since the first path of the lead 100 is often substantially linear which can have very little resistance to migration.

Figure 12:
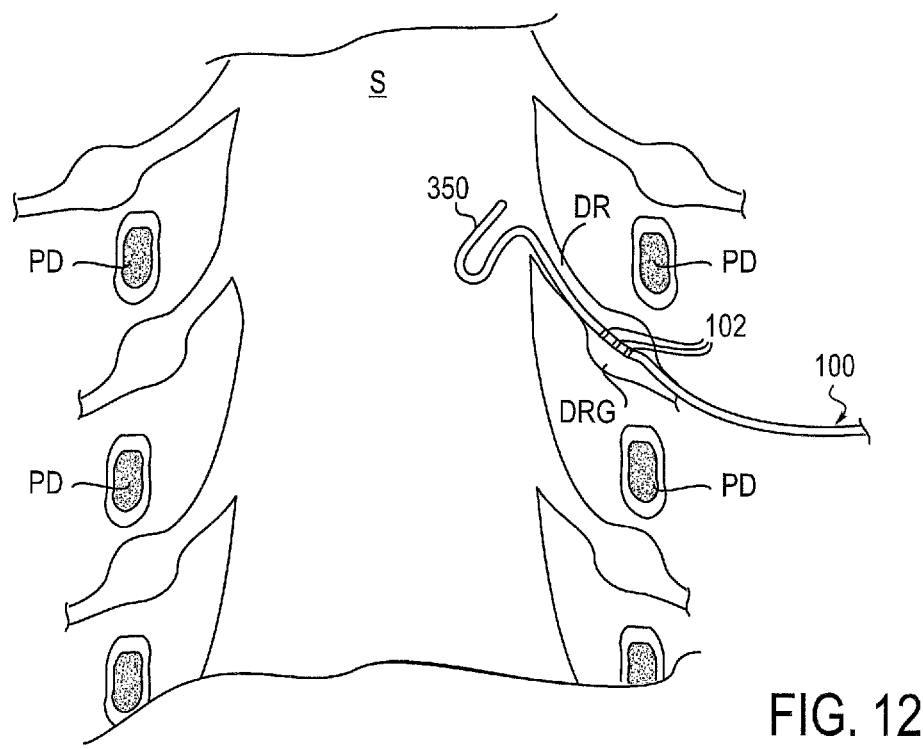
FIG. 12 illustrates an embodiment of a lead having slack anchor formed by an elongated tip.

FIG. 12 illustrates an embodiment of a lead 100 which has been positioned with a transforaminal/extraforaminal approach, wherein the DRG is approached from outside of the spinal column. In this embodiment, the lead 100 has an elongated distal tip 350 so that the distal tip 350 extends into the area of the spinal cord S while the at least one electrode 102 resides in proximity to the DRG. Here, the slack anchor is formed by the elongated distal tip 350 so as to anchor the lead 100 within the epidural space. Such a slack anchor may be formed with any of the techniques described above, such as with the use of the sheath 122 and/or stylet 124.

It may also be appreciated that the slack anchors of the present invention may be formed by leads and devices provided in U.S. Provisional Patent Application No. 61/178, 847, entitled "Methods, Systems and Devices for Delivering Stimulation to Spinal Anatomy, filed on May 15, 2009, incorporated herein by reference for all purposes. Likewise, the slack anchors of the present invention may be used to anchor such leads and devices positioned with the methods described therein.

Figure 13:
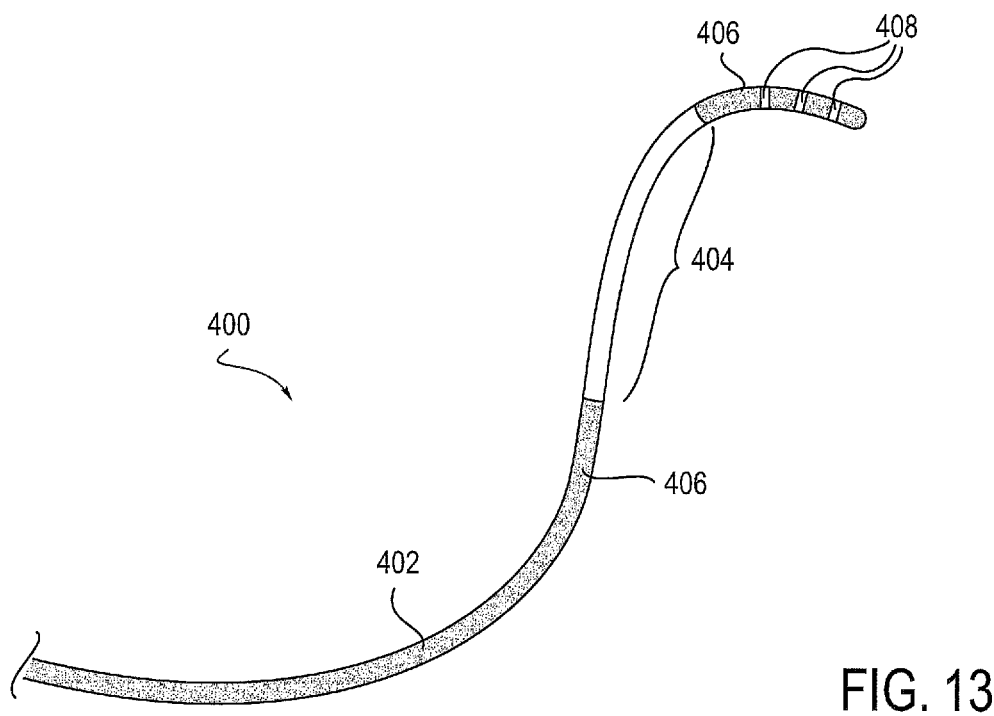
FIG. 13 illustrates an embodiment of a lead comprising a shaft having areas of differing stiffness.

In some embodiments, a modified lead 400 is used to create a slack anchor. In these embodiments, the lead 400 includes a structural kink point or bend area which assists in the creation of the slack anchor. For example, in some embodiments the structural kink point comprises a geometric feature, such as uv-notch. In other embodiments, the kink point comprises a change in material stiffness. For example, in some embodiments, the lead 400 comprises a shaft 402 having areas of differing stiffness, such as illustrated in FIG. 13. Here, the shaft 402 includes a flexible region 404 disposed between more rigid regions 406 (indicated by shading). Since the flexible region 404 is the area within which the slack anchor will be formed, the flexible region 404 is typically located proximal and close to the at least one electrode 408. Thus, the at least one electrode 408 will be anchored close to the target stimulation site.

Figure 14A:
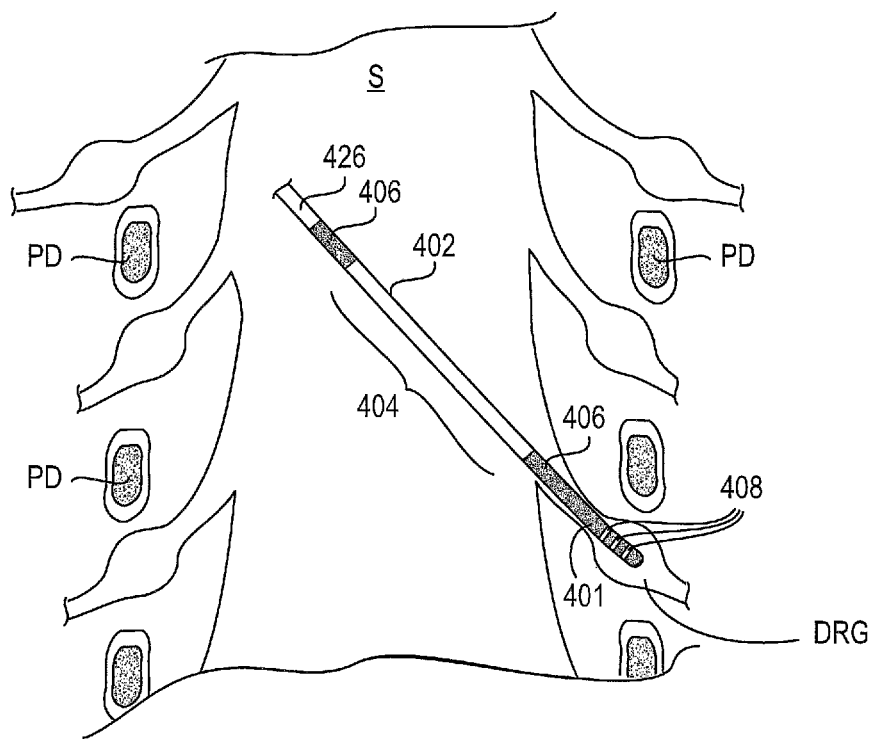
FIGS. 14A-14B illustrate an embodiment of a method of creating a slack anchor using the lead of FIG. 13.
Figure 14B:
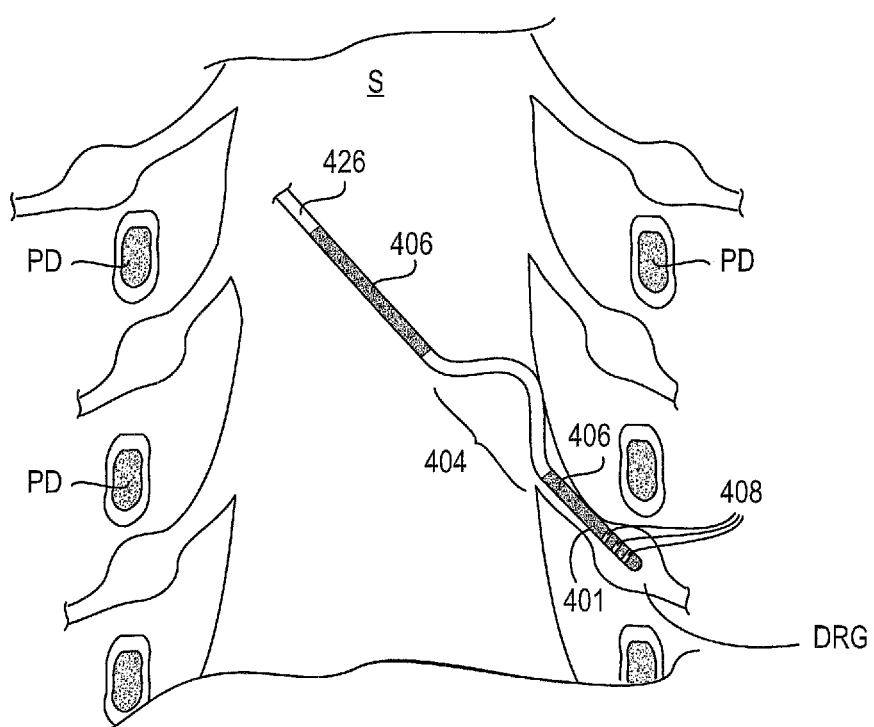

FIG. 14A illustrates the lead of FIG. 13 positioned near a target treatment site, in this instance a DRG. In this embodiment, the lead 400 is delivered to the DRG from a contralateral approach. The epidural space is accessed with the use of an introducing needle 426 and the lead 400 is advanced toward the target DRG so that the at least one electrode 408 is desirably positioned in relation to the target DRG. Thus, the distal end 401 of the lead 400 is positioned at the target location and the shaft 402 extends along a first path. Referring to FIG. 14B, the shaft 402 is then advanced through the introducing needle 426 along the first path due to the rigidity of the proximal more rigid region 406. However, this force is not significantly translated to the distal end 401 of the lead 400 due to the flexible region 404 therebetween, and the flexible region 404 bends or curves along a second path which typically includes portions which are lateral to the first path. Thus, the flexible region 404 forms a slack anchor and resists translation of motion to the distal end 401 of the lead 400. This assist in anchoring and prevention of lead migration.

It may be appreciated that forming a slack anchor in this manner, without the use of a sheath and/or stylet, is typically a less controlled method. The bends and curves formed in the flexible region are typically a product of the lead configuration in combination with the anatomical environment, wherein the user has less control over the actual shape of the slack anchor. In contrast, formation of a slack anchor with the use of a sheath and/or stylet, as described above, allows the user detailed control over each contour of the slack anchor.

A change in material stiffness along a lead 400, such as described and illustrated in relation to FIG. 13, can be created by a variety of methods or techniques. In some embodiments, the lead 400 has a construction as described and illustrated in U.S. patent application Ser. No. 12/687,737, entitled "Stimulation Leads, Delivery Systems and Methods of Use", filed Jan. 14, 2010, incorporated herein by reference for all purposes. In particular, in some embodiments the shaft 402 of the lead 100 is comprised of single lumen tube formed from an extruded polymer, such as urethane. Additional elements, such as conductor cables and optionally a tensile element, extend through the single lumen tube. In such embodiments, the shaft 402 is potted with a harder material to create the more rigid regions 406 of the lead 400. When the shaft 402 is comprised of a soft durometer material, such as polyurethanes (e.g. Bionate, Pellethane) or silicone, the potting material is comprised of a material having a relatively higher stiffness, such as epoxy (e.g. Epotek). The potting material is injected or deposited within the single lumen tube, surrounding the elements extending therethrough, and allowed to harden. This potting material increases the stiffness of the lead 400 in the areas within which it is deposited. Therefore, specific more rigid regions 406 may be created anywhere along the lead 400. In some embodiments, the lead 400 is potted in all areas except for the area within which the slack anchor is formed. In other embodiments, the lead 40 is potted proximally, leaving the distal-most end of the lead unspotted and more flexible. For example, in some embodiment where the lead 400 has a length of approximately 40 cm, the most proximal 30 cm of the lead 400 are potted.

It may be appreciated that particular portions of the lead 400, such as the distal end 401, may be preformed into a curve so as to more easily access a DRG (particularly through an antegrade approach). Pre-curving of potted areas may be achieved by pre-curving the shaft 402 prior to hardening of the potting material therein so that the hardened potting material sets the precurvature. Such precurvature may be useful when delivering the lead 400 without the use of a sheath or stylet. In addition, in such embodiments the lead 400 may not include a stylet lumen which reduces the outer diameter, such as up to approximately 25-40%. Such reduction in diameter may increase the ability to access particular anatomy, such as stenosed foraminal openings or peripheral nerves.

In other embodiments, the shaft 402 is interoperatively tilled with a deployable curing polymer to create the more rigid regions 406 of the lead 400. Again, in some embodiments the shaft 402 of the lead 100 is comprised of single lumen tube formed from an extruded polymer, such as urethane. Additional elements, such as conductor cables and optionally a tensile element, extend through the single lumen tube. In such embodiments, the shaft 402 is injected with a polymer or other material that cures to create the more rigid regions 406 of the lead 400. This cured material increases the stiffness of the lead 400 in the areas within which it is deposited. Since the material is injected interoperatively, the user is able to determine the desired locations for the more rigid regions 406 based on the specific anatomy of the patient and on the particulars of the surgical procedure. Thus, the location and configuration of the slack anchor may be precisely individualized for the patient.

It may be appreciated that a change in material stiffness along a lead 400 can alternatively be created by a variety of other methods or techniques. For example, the wall of the shaft 402 may be reinforced in the more rigid regions 400, such as by a harder durometer material, a reinforcing braid or straight wire composite, co-extrusion with a second stiffer material, overmolding, or thickening of the wall, to name a few. Likewise, the shaft 402 may be comprised of a variety of materials, each having a different durometer. For example, the shaft 402 may be comprised of single lumen tube having a stiffer durometer in the more rigid regions 406 and a less stiff durometer in the flexible regions 404. There are several scales of durometer, each used for materials with different properties. The two most common scales, using slightly different measurement systems, are the ASTM D2240 type A and type D scales. The A scale is for softer plastics, while the D scale is for harder ones. However, the ASTM D2240-00 testing standard calls for a total of 12 scales, depending on the intended use: types A, B, C, D, DO, E, M, O, OO, OOO, OOO-S, and R. Each scale results in a value between 0 and 100, with higher values indicating a harder material. Thus, the use of materials having widely differing values, such as a "C" durometer 55 and 70, may be used to create a kink point according to the present invention.

In other embodiments, a change in material stiffness along the lead 400 is created by a separable stylet. In such embodiments, the stylet is first used to assist in positioning the lead 400, such as described above. Once the lead 400 has been desirably positioned, the stylet is separated, divided, disjoined or decoupled so as to leave a portion of the stylet within the lead 400 forming a more rigid region 406. The area having the stylet removed therefrom forms the flexible region 404. For example, in some embodiments the stylet extends to or near the distal tip of the lead 400 wherein the stylet is separable at a location proximal to the distal tip. The stylet is then pulled back a desired distance to create a flexible region wherein which a slack anchor is formable. The remainder of the stylet then resides proximal to this flexible region so as to create a lead having a change in material stiffness such as illustrated in FIG. 13. A slack anchor may then be created, such as according to methods similar to the methods illustrated in FIGS. 14A-14B. It may be appreciated that the stylet may be separable in a variety of locations so as to create various patterns of more rigid regions 406. It may also be appreciated that the stylet may be used for the purpose of creating material stiffness, without the use of positioning the lead.

Similarly, in some embodiments a change in material stiffness along the lead 400 is created by a separable sheath. In such embodiments, the sheath is first used to assist in positioning the lead 400, such as described above. Once the lead 400 has been desirably positioned, the sheath is separated, divided, disjoined or decoupled so as to leave a portion of the sheath along the lead 400 forming a more rigid region 406. The area having the sheath removed therefrom forms the flexible region 404. For example, in some embodiments the sheath extends near the distal tip of the lead 400 proximal to the electrodes, wherein the sheath is separable at a location proximal to the distal end of the sheath. The sheath is then pulled back a desired distance to create a flexible region wherein which a slack anchor is formable. The remainder of the sheath then resides proximal to this flexible region. A slack anchor may then be created, such as according to methods similar to the methods illustrated in FIGS. 14A-44B. It may be appreciated that the sheath may be separable in a variety of locations so as to create various patterns of more rigid regions 406. It may also be appreciated that the sheath may be used for the purpose of creating material stiffness, without the use of positioning the lead.

It may be appreciated that the devices, systems and methods described herein may be used to reduce lead migration in leads targeting any portion of the nervous system. Leads may be positioned so as to stimulate portions of the central nervous system, such as the spinal cord, spinal nerves, and brain. Likewise, leads may be positioned so as to stimulate portions of the peripheral nervous system. In particular, leads may be positioned as described in U.S. Provisional Patent Application No. 61/473,132 entitled "Devices, Systems and Methods for Modulation of the Nervous System," filed Apr. 7, 2011, incorporated herein by reference for all purposes. To reduce the potential for lead migration in any of these lead positions, a slack anchor may be formed along the lead according to any of the methods described herein. Such a slack anchor may be positioned within the epidural space. Or, the slack anchor may be formed outside of the epidural space. In some embodiments, when creating a slack anchor in tissue outside of the epidural space, a virtual space is created in the tissue with the use of a variety of space generating techniques, such as with the use of expanders, retractors, dissectors, tunneling tools, and insufflators to name a few. The slack anchor is then created within the virtual space providing strain relief and anchoring capabilities which assist in maintaining the position of the distal end of the lead near the target tissue. In other embodiments, when creating a slack anchor in tissue outside of the epidural space, naturally existing spaces are utilized for positioning a slack anchor therein.

Although the foregoing invention has been described in some detail by way of illustration and example, for purposes of clarity of understanding, it will be obvious that various alternatives, modifications, and equivalents may be used and the above description should not be taken as limiting, in scope of the invention which is defined by the appended claims.

All publications and patent applications mentioned in this specification are herein incorporated by reference to the same extent as if each individual publication or patent application was specifically and individually indicated to be incorporated by reference.

The invention claimed is:

1. A method of positioning a lead to electrically stimulate a dorsal root ganglion of a patient, the method comprising:
    advancing a distal end of the lead with a stylet from an entry point into an epidural space of the patient;
    advancing a sheath over the lead such that a first distal end of the sheath is proximate the distal end of the lead to cause the lead to follow a first curvature of the first distal end of the sheath;
    advancing the lead, the sheath, and the stylet from the epidural space to a position wherein electrodes of the lead are positioned proximate to the dorsal root ganglion, wherein a second curvature of the stylet within the lead causes the lead to bend along a nerve root angulation of the dorsal root ganglion;
    after the lead is positioned with electrodes proximate to the dorsal root ganglion, introducing an additional portion of a shaft of the lead into the epidural space with the stylet withdrawn from the additional portion of the shaft, wherein the additional portion of the shaft of the lead forms an undulating or loop shape in the epidural space; and
    connecting the lead to an implantable pulse generator to provide electrical stimulation to the dorsal root ganglion wherein the undulating or loop shape of the additional portion of the shaft of the lead forms a slack anchor between electrodes of the lead and the entry point.

2. The method of claim 1, wherein the shaft of the lead comprises a kink point to assist formation of the undulating or loop shape in the epidural space.

3. The method of claim 1, wherein the undulating or loop shape of the additional portion of the shaft of the lead forms multiple switchbacks between the dorsal root ganglion and the entry point.

4. The method of claim 1, wherein the lead is advanced into the epidural space through an introducer sheath.

5. The method of claim 4, wherein the introducer sheath comprises a tip that is adapted to direct the additional portion of the shaft to form the undulating or loop shape in the epidural space.

6. The method of claim 1, wherein the lead comprises a lead body of a soft pliant polymer material, without a mechanical bias to assume a predetermined shape.

7. The method of claim 1, wherein the additional portion of the shaft is more flexible than the distal end of the lead to cause the additional portion of the shaft to form the undulating or loop shape in the epidural space.

8. The method of claim 7, wherein the undulating or loop shape is formed without displacing the electrodes from a location proximate to the dorsal root ganglion.

9. The method of claim 1, wherein the electrical stimulation is delivered to the dorsal root ganglion through electrodes of the lead.

10. The method of claim 1, wherein the slack anchor is adapted to reduce risk of migration for the lead in the epidural space.

11. The method of claim 1, wherein the lead is advanced from the epidural space to the position through a foramen.

12. The method of claim 1, the method further comprising:
    advancing the distal end of the lead beyond the distal end of the sheath prior to withdrawal of the stylet, wherein a first flexibility of the distal end of the lead exceeds a second flexibility of the first distal end of the sheath, and wherein a difference between the first flexibility and the second flexibility causes the shaft of the lead to bend thereby forming a kink.

13. The method of claim 12, wherein the kink is configured to prevent a migration of the lead so that the distal end of the lead maintains the position wherein electrodes of the lead are positioned proximate to the dorsal root ganglion.

14. The method of claim 13, wherein frictional forces between the kink and the epidural space prevent the migration of the lead.

15. The method of claim 1, the method further comprising:
partially withdrawing the sheath before introducing the additional portion of the shaft of the lead into the epidural space.

* * * * *

UNITED STATES PATENT AND TRADEMARK OFFICE
CERTIFICATE OF CORRECTION

Page 1 of 1

PATENT NO. : 11,413,451 B2
APPLICATION NO. : 16/579389
DATED : August 16, 2022
INVENTOR(S) : Eric J. Grigsby et al.

It is certified that error appears in the above-identified patent and that said Letters Patent is hereby corrected as shown below:

In the Specification

At Column 5, Line number 51, delete "(FIG. 28)" and replace with --(FIG. 2B)--.
At Column 6, Line number 1, delete "FIG. 20" and replace with --FIG. 2C--.
At Column 6, Line number 11, delete "sty/et" and replace with --stylet--.
At Column 6, Line number 20, delete "target OR" and replace with --target DRG--.
At Column 7, Line number 38, delete "path Referring" and replace with --path. Referring--.
At Column 9, Line number 20, delete "shalt 101" and replace with --shaft 101--.
At Column 10, Line number 4, delete "few, FIG. 11" and replace with --few. FIG. 11--.
At Column 12, Line number 14, delete "regions 400" and replace with --regions 406--.
At Column 13, Line number 9, delete "FIGS. 14A-44B" and replace with --FIGS. 14A-14B--.

Signed and Sealed this
Twenty-second Day of November, 2022

Katherine Kelly Vidal
*Director of the United States Patent and Trademark Office*